US005922550A

United States Patent [19]

Everhart et al.

[11] Patent Number: 5,922,550

[45] Date of Patent: Jul. 13, 1999

[54] BIOSENSING DEVICES WHICH PRODUCE DIFFRACTION IMAGES

[75] Inventors: Dennis S. Everhart, Alpharetta, Ga.; Michael Grunze, Neckargemuend, Germany; Rosann Marie Kaylor, Cumming, Ga.; Friderike Karolin Deseree Morhard, Heidelberg, Germany

[73] Assignee: Kimberly-Clark Worldwide, Inc., Neenah, Wis.

[21] Appl. No.: 08/768,449

[22] Filed: Dec. 18, 1996

[51] Int. Cl.[6] .................................................. G01N 33/567

[52] U.S. Cl. ......................... 435/7.21; 435/291; 436/501; 536/120

[58] Field of Search .................................. 435/7.29, 291; 156/655.1

[56] References Cited

U.S. PATENT DOCUMENTS

| | | | |
|---|---|---|---|
| 4,363,874 | 12/1982 | Greenquist | 435/7 |
| 4,562,157 | 12/1985 | Lowe et al. | 435/291 |
| 4,596,697 | 6/1986 | Ballato | 422/98 |
| 4,690,715 | 9/1987 | Allara et al. | 148/6.15 |
| 4,837,715 | 6/1989 | Ungpiyakul et al. | 364/552 |
| 4,844,613 | 7/1989 | Batchelder et al. | 356/318 |
| 4,851,816 | 7/1989 | Macias et al. | 340/573 |
| 4,877,747 | 10/1989 | Stewart | 436/525 |
| 4,992,385 | 2/1991 | Godfrey | 436/525 |
| 5,023,053 | 6/1991 | Finlan | 422/82.05 |
| 5,035,863 | 7/1991 | Finlan et al. | 422/82.05 |
| 5,055,265 | 10/1991 | Finlan | 422/82.05 |
| 5,063,081 | 11/1991 | Cozzette et al. | 435/4 |
| 5,064,619 | 11/1991 | Finlan | 422/82.05 |
| 5,143,854 | 9/1992 | Pirrung et al. | 436/518 |
| 5,182,135 | 1/1993 | Giesecke et al. | 427/98 |
| 5,189,902 | 3/1993 | Groeninger | 73/24.06 |
| 5,190,350 | 3/1993 | Backman | 436/501 |
| 5,235,238 | 8/1993 | Nomura et al. | 310/349 |
| 5,242,828 | 9/1993 | Bergstrom et al. | 435/291 |
| 5,268,306 | 12/1993 | Berger | 436/527 |
| 5,327,225 | 7/1994 | Bender et al. | 356/445 |
| 5,334,303 | 8/1994 | Muramatsu et al. | 204/412 |
| 5,374,563 | 12/1994 | Maule | 436/165 |
| 5,402,075 | 3/1995 | Lu et al. | 324/664 |
| 5,404,756 | 4/1995 | Briggs et al. | 73/718 |
| 5,415,842 | 5/1995 | Maule | 422/82.05 |
| 5,436,161 | 7/1995 | Bergstrom et al. | 435/291 |
| 5,451,683 | 9/1995 | Barrett et al. | 548/302.7 |
| 5,455,475 | 10/1995 | Josse et al. | 310/316 |
| 5,482,867 | 1/1996 | Barrett et al. | 436/518 |
| 5,489,678 | 2/1996 | Fodor et al. | 536/22.1 |
| 5,510,481 | 4/1996 | Bednarski | 536/120 |
| 5,512,131 | 4/1996 | Kumar et al. | 156/655.1 |
| 5,514,559 | 5/1996 | Markert-Hahn et al. | 435/7.92 |
| 5,580,697 | 12/1996 | Keana et al. | 430/296 |
| 5,643,681 | 7/1997 | Voorhees et al. | 428/483 |
| 5,658,443 | 8/1997 | Yamamoto et al. | 204/403 |

FOREIGN PATENT DOCUMENTS

| | | |
|---|---|---|
| 2273772 | 6/1994 | United Kingdom . |
| WO 96/29629 | 9/1996 | WIPO . |
| 9633971 | 10/1996 | WIPO . |

OTHER PUBLICATIONS

Mrksich et al., "Patterning self–assembled monolayers using microcontact printing: A new technology for biosensors?", Tibtech, vol. 13, pp. 228–235 (1995).

Abbott et al., Using Micromachining, Molecular Self–Assembly, and Wet Etching to Fabricate 0.1–1 μm–Scale Structures of Gold and Silicon, Chemistry of Materials, vol. 6, No. 5, pp. 596–602 (1994).

Jeon et al., "Patterned Self–Assembled Monolayers Formed by Microcontact Printing Direct Selective Metalization by Chemical Vapor Deposition on Planar and Nonplanar Substrates", Langmuir, vol. 11, No. 8, pp. 3024–3026 (1995).

Kim et al., "Combining Patterned Self–Assembled Monolayers of Alkanethiolates on Gold with Anisotropic Etching of Silicon to Generate Controlled Surface Morphologies", J. Electrochem. Soc., vol. 142, No. 2, pp. 628–633 (Feb. 1995).

Folkers et al., "Self–Assembled Monolayers of Long–Chain Hydroxamic Acids on the Native Oxides of Metals", Langmuire, vol. 11, No. 3, pp. 813–824 (1995).

Kumar et al., "Patterned Condensation Figures as Optical Diffraction Gratings", Science, vol. 263, pp. 60–62. (Jan. 7, 1994).

Wilbur et al., "Microfabrication by Microcontact Printing of Self–Assembled Monolayers", Adv. Mater., vol. 6, No. 7/8, pp. 600–604 (1994).

Kelkar et al., "Acoustic Plate Waves for Measurement of Electrical Properties of Liquids", Microchem. Journal, vol. 43, pp. 155–164 (1991).

Liedberg et al, "Molecular Gradients of ω–Substituted Alkanethiols on Gold: Preparation and Characterization", Langmuir, vol. 11, pp. 3821–3827 (1995).

Shana et al, "Analysis of electrical equivalent circuit of quartz crystal resonator loaded with viscous conductive liquids", Journal of Electroanalytical Chemistry, vol. 379, pp. 21–33 (1994).

Shana et al, "Quartz Crystal Resonators as Sensors in Liquids Using the Acoustoelectric Effect", Anal. Chem., vol. 66, pp. 1955–1964 (1994).

(List continued on next page.)

*Primary Examiner*—Christopher L. Chin
*Assistant Examiner*—Ginny Allen Portner
*Attorney, Agent, or Firm*—Jones & Askew, LLP

[57] ABSTRACT

The present invention provides an inexpensive and sensitive device and method for detecting and quantifying analytes present in a medium. The device comprises a metalized film upon which is printed a specific, predetermined pattern of a analyte-specific receptors. Upon attachment of a target analyte to select areas of the plastic film upon which the receptor is printed, diffraction of transmitted and/or reflected light occurs via the physical dimensions and defined, precise placement of the analyte. A diffraction image is produced which can be easily seen with the eye or, optionally, with a sensing device.

52 Claims, 16 Drawing Sheets

OTHER PUBLICATIONS

Kumar et al., "Features of gold having micrometer to centimeter dimensions can be formed through a combination of stamping with an elastomeric stamp and an alkanethiol "ink" following by chemical etching", Appl. Phys. Lett., vol. 63, pp. 2002–2004 (1993).

Josse et al., "Electrical Surface Perturbation of a Piezoelectric Acoustic Plate Mode by a Conductive Liquid Loading", IEEE Transactions on Ultrasonics, Ferroelectrics, and Frequency Control, vol. 39, No. 4, (Jul. 1992).

Josse et al., "On the use of ZX–LiNbO3 acoustic plate mode devices as detectors for diulte electrolytes", Sensors and Actuators B, vol. 9, pp. 97–112 (1992).

Daphint et al., "Probing of strong and weak electrolytes with acoustic wave fields", Sensors and Actuators B, vol. 9, pp. 155–162 (1992).

Kumar et al., "Patterning Self–Assembled Monolayers: Applications in Materials Science", Langmuir, vol. 10, pp. 1498–1511 (1994).

Seah, M.P. "Quantitative Prediction of Surface Segregation", Journal of Catalysis, vol. 57, pp. 450–457 (1979).

Tsai et al., "Comment on the Prediction of Segregation to Alloy Surfaces", Journal of Catalysis—Letters to the Editor, vol. 50, pp. 200–202 (1977).

Burton et al. "Prediction of Segregation to Alloy Surfaces from Bulk Phase Diagram", Phys. Rev. Letter, vol. 37, No. 21, pp. 1433–1436 (Nov. 22, 1976).

Johnson et al. "Orientation dependence of surface segregation in a dilute Ni–Au alloy", J. Vac. Sci. Technol., vol. 15, No. 2, pp. 467–469 (Mar./Apr. 1978).

Osada et al., "Intelligent Gels", Scientific American, pp. 82–87, May 1993.

Saito et al., "Volume Phase Transition of N–Alkylacrylamide Gels", Advances on Polymer Science, vol. 109, pp. 207–232 (1993).

Okano T. "Molecular Design of Temperature–Responsive Polymers as Intelligent Materials", Advances in Polymer Science, vol. 110, pp. 179–197 (1993).

Shibayama et al., "Volume Phase Transition and Related Phenomena of Polymer Gels", Advances in Polymer Science, vol. 109, pp. 1–62 (1993).

Kokufuta, E. "Novel Applications for Stimulus–Sensitive Polymer Gels in the Preparation of Functional Immobolized Biocatalysts", Advances in Polymer Science, vol. 110, pp. 157–177 (1993).

Osada et al, "Stimuli–Responsive Polymer Gels and Their Application to Chemomechanical Systems", Prog. Polym. Sci., vol. 18, pp. 187–226 (1993).

Irie, M. "Stimuli–Resposnsive Poly(N–isopropylacrylamide) Photo–and Chemical–Induced Phase Transitions", Advances in Polymer Science, vol. 110, pp. 49–65 (1993).

Bhatia, S.K. et al, Analytical Biochem., vol. 208, pp. 197–205, 1993.

Häussling, L. et al, Angew. Chem. Int. Ed. Engl., vol. 30, No. 5, 1991, pp. 569–572.

Muller, W et al, Science, vol. 262, Dec. 10, 1993, pp.1706–1708.

Jennane, J. et al, Can. J. Chem., vol. 74, 1996, pp. 2509–2517.

Diamandis, E P et al, Clin. Chem., vol. 37(5), 1991, pp. 625–636.

Bhatia, S.K. et al, 1992, J. Am. Chem. Soc., vol. 114, p. 4432.

Fig. 4a
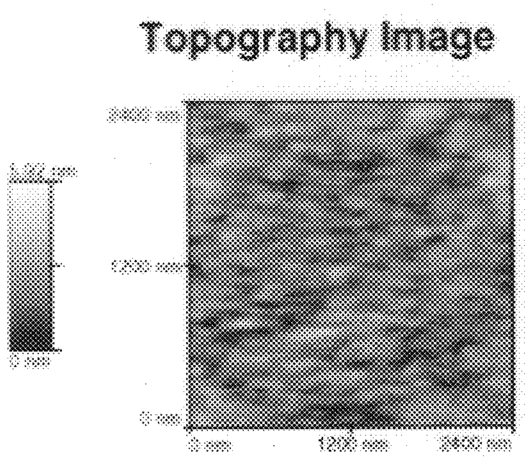
Fig. 4b
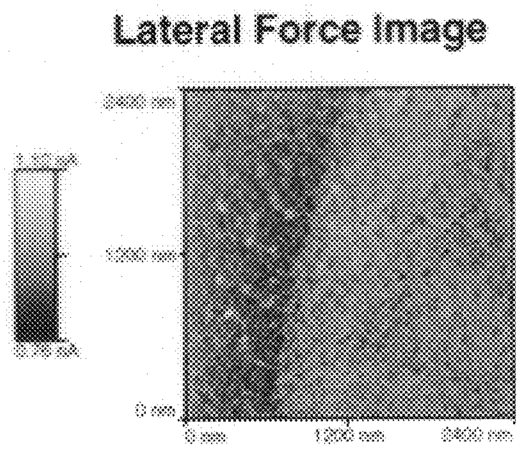
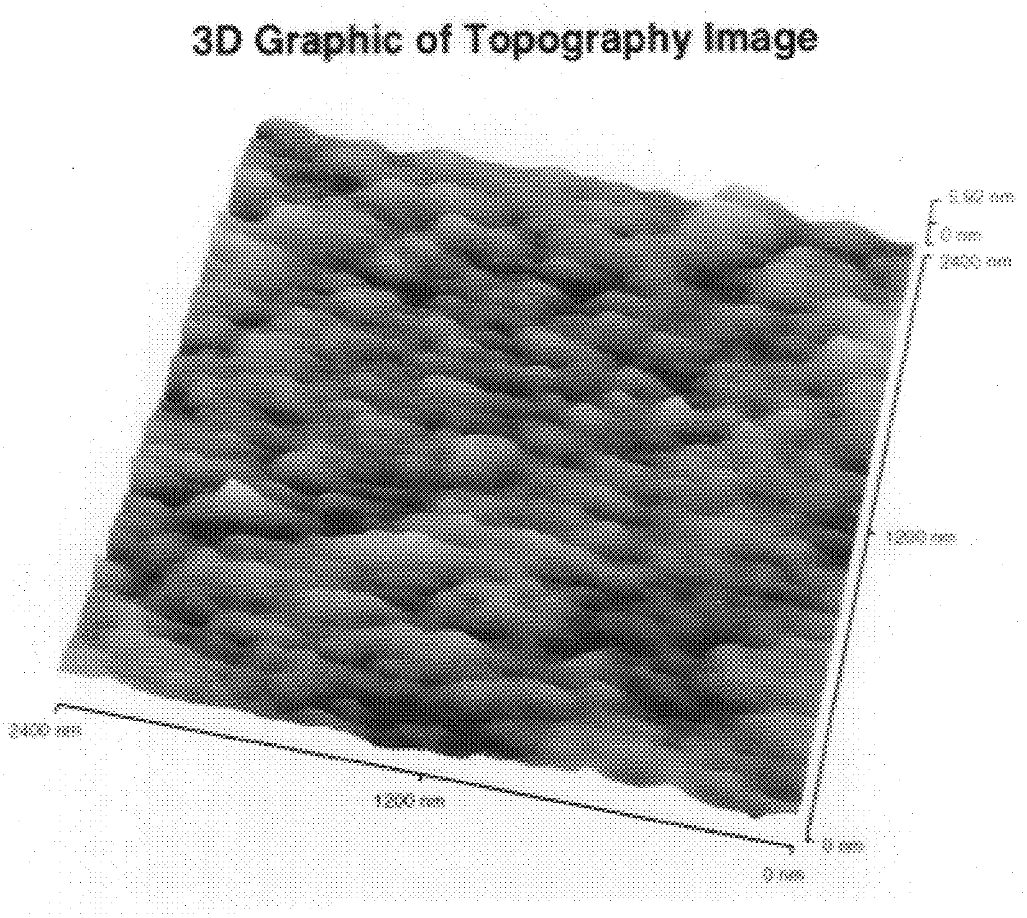
Fig. 4c

BIOSENSING DEVICES WHICH PRODUCE DIFFRACTION IMAGES

TECHNICAL FIELD

The present invention is generally in the field of detecting analytes in a medium and, more particularly, the present invention relates to micro-contact printing of analyte-specific receptors onto metalized plastic film for the development of single use, disposable sensors to indicate the presence of the analyte in a medium.

BACKGROUND OF THE INVENTION

There are many systems and devices available for detecting a wide variety of analytes in various media. Most of these systems and devices are relatively expensive and require a trained technician to perform the test. There are many cases where it would be advantageous to be able to determine if an analyte were present in a large number of samples. A good example of this type of need is in food packaging. Currently, food samples are randomly checked for microbial contamination by conventional assay techniques. Although this method of sampling will indicate trends among a population of samples, it does not test every sample in a population. What is needed is an inexpensive and accurate method of testing every sample in use.

Sandstrom et al., 24 *Applied Optics* 472, 1985, describe use of an optical substrate of silicon with a layer of silicon monoxide and a layer of silicon formed as dielectric films. They indicate that a change in film thickness changes the properties of the optical substrate to produce different colors related to the thickness of the film. The thickness of the film is related to the color observed and a film provided on top of an optical substrate may produce a visible color change. The authors indicate that a mathematical model can be used to quantitate the color change, and that "[c]alculations performed using the computer model show that very little can be gained in optical performance from using a multilayer structure . . . but a biolayer on the surface changes the reflection of such structures very little since the optical properties are determined mainly by the interfaces inside the multilayer structure. The most sensitive system for detection of biolayers is a single layer coating, while in most other applications performance can be by additional dielectric layers."

Sandstrom et al., go on to indicate that slides formed from metal oxides on metal have certain drawbacks, and that the presence of metal ions can also be harmful in many biochemical applications. They indicate that the ideal top dielectric film is a 2–3 nm thickness of silicon dioxide which is formed spontaneously when silicon monoxide layer is deposited in ambient atmosphere, and that a 70–95 nm layer silicon dioxide on a 40–60 nm layer of silicon monoxide can be used on a glass or plastic substrate. They also describe formation of a wedge of silicon monoxide by selective etching of the silicon monoxide, treatment of the silicon dioxide surface with dichlorodimethylsilane, and application of a biolayer of antigen and antibody. From this wedge construction they were able to determine film thickness with an ellipsometer, and note that the "maximum contrast was found in the region about 65 nm where the interference color changed from purple to blue." They indicate that the sensitivity of such a system is high enough for the detection of protein antigen by immobilized antibodies. They conclude "the designs given are sensitive enough for a wide range of applications. The materials, i.e., glass, silicon, and silicon oxides, are chemically inert and do not affect the biochemical reaction studied. Using the computations above it is possible to design slides that are optimized for different applications. The slides can be manufactured and their quality ensured by industrial methods, and two designs are now commercially available.

U.S. Pat. No. 5,482,830 to Bogart, et al., describes a device that includes a substrate which has an optically active surface exhibiting a first color in response to light impinging thereon. This first color is defined as a spectral distribution of the emanating light. The substrate also exhibits a second color which is different from the first color (by having a combination of wavelengths of light which differ from that combination present in the first color, or having a different spectral distribution, or by having an intensity of one or more of those wavelengths different from those present in the first color). The second color is exhibited in response to the same light when the analyte is present on the surface. The change from one color to another can be measured either by use of an instrument, or by eye. Such sensitive detection is an advance over the devices described by Sandstrom and Nygren, supra, and allow use of the devices in a commercially viable and competitive manner.

However, the method and device described in the Bogart, et al. patent has several disadvantages. One disadvantage is the high cost of the device. Another problem with the device is the difficulty in controlling the various layers that are placed on the wafer so that one obtains a reliable reading. What is needed is a biosensor device that is easy and inexpensive to manufacture and is capable of reliable and sensitive detection of the analyte to be detected.

SUMMARY OF THE INVENTION

The present invention provides an inexpensive and sensitive device and method for detecting and quantifying analytes present in a medium. The device comprises a metalized film upon which is printed a specific predetermined pattern of a analyte-specific receptors. Upon attachment of a target analyte, which is capable of scattering light, to select areas of the plastic film upon which the receptor is printed, diffraction of transmitted and/or reflected light occurs via the physical dimensions and defined, precise placement of the analyte. A diffraction image is produced which can be easily seen with the eye or, optionally, with a sensing device. By "diffraction" it is meant the phenomenon, observed when waves are obstructed by obstacles, of the disturbance spreading beyond the limits of the geometrical shadow of the object. The effect is marked when the size of the object is of the same order as the wave length of the waves. In the present invention, the obstacles are analytes and the waves are light waves.

The present invention utilizes methods of contact printing of patterned, self-assembling monolayers of alkanethiolates, carboxylic acids, hydroxamic acids, and phosphonic acids on metalized thermoplastic films, the compositions produced thereby, and the use of these compositions. The self-assembling monolayers have receptive materials bound thereto. The receptive materials are specific for a particular analyte or class of analytes depending upon the receptor used. The methods for contact printing of patterned, self assembling monolayers are disclosed fully in U.S. patent application Ser. Nos. 08/707,456 and 08/769,594, both of which are incorporated herein by reference in their entirety.

Patterned self-assembling monolayers allow for the controlled placement of analytes thereon via the patterns of analyte-specific receptors. The biosensing devices of the present invention produced thereby are used by first exposing the biosensing device to a medium that contains the analyte of choice and then, after an appropriate incubation period, transmitting a light, such as a laser, through the film. If the analyte is present in the medium and is bound to the receptors on the patterned self-assembling monolayer, the light is diffracted in such a way as to produce a visible image. In other words, the patterned self-assembling monolayers with the analyte bound thereto can produce optical diffraction patterns which differ depending on the reaction of the receptors on the self-assembling monolayer with the analyte of interest. The light can be in the visible spectrum, and be either reflected from the film, or transmitted through it, and the analyte can be any compound or particle reacting with the self-assembling monolayer. The light can be a white light or monochromatic electromagnetic radiation in the visible region. The present invention also provides a flexible support for a self-assembling monolayer on gold or other suitable metal or metal alloy.

The present invention includes a support for a self-assembling monolayer on gold or other suitable material which does not require an adhesion promoter for the formation of a well-ordered self-assembling monolayer. The present invention also provides a support for a self-assembling monolayer on gold or other material which is suitable for continuous printing, rather than batch, fabrication. In addition, the present invention provides a low-cost, disposable biosensor which can be mass produced. The biosensors of the present invention can be produced as a single test for detecting an analyte or it can be formatted as a multiple test device. The biosensors of the present invention can be used to detect contamination in garments, such as diapers, and to detect contamination by microorganisms.

In another embodiment of the present invention, nutrients for a specific class of microorganisms can be incorporated into the self assembling monolayer. In this way, very low concentrations of microorganisms can be detected by first contacting the biosensor of the present invention with the nutrients incorporated therein and then incubating the biosensor under conditions appropriate for the growth of the bound microorganism. The microorganism is allowed to grow until there are enough organisms to form a diffraction pattern.

The present invention can also be used on contact lenses, eyeglasses, window panes, pharmaceutical vials, solvent containers, water bottles, bandaids, and the like to detect contamination.

These and other features and advantages of the present invention will become apparent after a review of the following detailed description of the disclosed embodiments.

BRIEF DESCRIPTION OF THE FIGURES

FIGS. 4*a*, 4*b* and 4*c* are atomic force microscopy images of a hydrophilic self-assembling monolayer circle of 16 mercaptohexadecanoic acids, as described in Example 1. FIG. 4*a* is a topography image, FIG. 4*b* is a lateral force image, and FIG. 4*c* is a three-dimensional graphic of a topography image.

DETAILED DESCRIPTION

Figure 1:
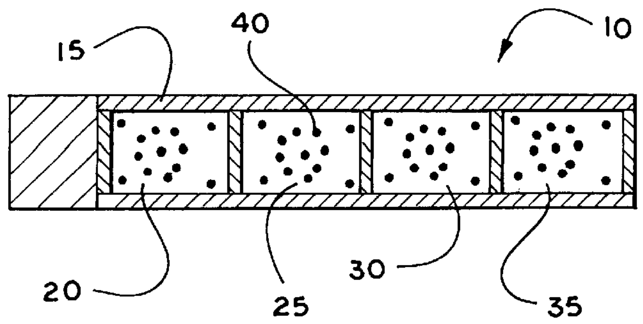
FIG. 1 shows a biosensor capable of simultaneously measuring several different analytes in a medium.

The present invention features improved biosensing devices, and methods for using such biosensing devices, for detecting and quantifying the presence or amount of an analyte of interest within a medium. The analytes that can be detected by the present invention include, but are not limited to, microorganisms such as bacteria, yeasts, fungi and viruses. In contrast to prior devices, those of the present invention allow detection of extremely small quantities of analyte in a medium in a rapid assay lasting only a few minutes. In addition, no signaling or associated electronic components are required in the biosensing devices of the present invention.

The present invention comprises micro-contact printing of analyte-specific receptors onto metalized plastic film which allows for the development of single use, disposable biosensors based on light diffraction to indicate the presence of the analyte. Upon attachment of a target analyte to select areas of the plastic film which contain the receptor, diffraction of transmitted and/or reflected light occurs via the physical dimensions and defined, precise placement of the analyte. For example, yeast, fungi or bacterium are large enough to act as diffraction elements for visible light when placed in organized patterns on a surface. In addition to producing a simple diffraction image, patterns of analytes can be such as to allow for the development of a holographic sensing image and/or a change in visible color. Thus, the appearance of a hologram or a change in an existing hologram will indicate a positive response. The pattern made by the diffraction of the transmitted light can be any shape including, but not limited to, the transformation of a pattern from one pattern to another upon binding of the analyte to the receptive material. In particularly preferred embodiments, the diffraction pattern is discernible in less than one hour after contact of the analyte with the biosensing device of the present invention.

The diffraction grating which produces the diffraction of light upon interatction with the analyte must have a minimum periodicity of ½ the wavelength and a refractive index different from that of the surrounding medium. Very small analytes, such as viruses or molecules, can be detected indirectly by using a larger particle that is specific for the small analyte. In one embodiment in which the small analyte can be detected comprises coating the particle, such as a latex bead, with a receptive material that specifically binds to the analyte of interest. Particles that can be used in the present invention include, but are not limited to, glass, cellulose, synthetic polymers or plastics, latex, polystyrene, polycarbonate, proteins, bacterial or fungal cells and the like. The particles are preferably spherical in shape, but the structural and spatial configuration of the particles is not critical to the present invention. For instance, the particles could be slivers, ellipsoids, cubes, and the like. A desirable particle size ranges from a diameter of approximately 02 $\mu$m to 50.0 $\mu$m, desirably between approximately 0.4 $\mu$m to 1 $\mu$m. The composition of the particle is not critical to the present invention.

The self-assembling monolayer on the metalized film contains a receptive material, such as an antibody, that will specifically bind to an epitope on the analyte that is different from the epitope used in the binding to the particle. Thus, for detecting a medium with a small analyte, such as viral particles, the medium is first exposed to the latex particles to which the viral particles bind. Then, the latex particles are optionally washed and exposed to the metalized film with the self-assembling monolayers containing the virus specific antibodies. The antibodies then bind to the viral particles on the latex bead thereby immobilizing the latex beads in the same pattern as the monolayers on the film. Because the bound latex beads will cause diffraction of the visible light, a diffraction pattern is formed, indicating the presence of the viral particle in the liquid. Other combinations using particles are well known to those of ordinary skill in the art.

The analytes that are contemplated as being detected using the present invention include, but are not limited to, bacteria; yeasts; fungi; viruses; rheumatoid factor; antibodies, including, but not limited to IgG, IgM, IgA and IgE antibodies; carcinoembryonic antigen; streptococcus Group A antigen; viral antigens; antigens associated with autoimmune disease, allergens, tumor antigens; streptococcus Group B antigen, HIV I or HIV II antigen; or host response (antibodies) to these and other viruses; antigens specific to RSV or host response (antibodies) to the virus; an antibody; antigen; enzyme; hormone; polysaccharide; protein; lipid; carbohydrate; drug or nucleic acid; Salmonella species; Candida species, including, but not limited to *Candida albicans* and *Candida tropicalis;* Salmonella species; *Neisseria meningitides* groups A, B, C, Y and W sub 135, *Streptococcus pneumoniae, E. coli* K1, *Haemophilus influenza* type B; an antigen derived from microorganisms; a hapten, a drug of abuse; a therapeutic drug; environmental agents; and antigens specific to Hepatitis.

In another embodiment of the present invention, nutrients for a specific class of microorganisms can be incorporated into the self assembling monolayer. In this way, very low concentrations of microorganisms can be detected by first contacting the biosensor of the present invention with the nutrients incorporated therein and then incubating the biosensor under conditions appropriate for the growth of the bound microorganism. The microorganism is allowed to grow until there are enough organisms to form a diffraction pattern. Of course, in some cases, the microorganism can multiply enough to form a diffraction pattern without the presence of a nutrient on the patterned monolayer.

A part of the present invention is a receptive material that can be microprinted on the metalized film and will specifically bind to the analyte of interest. Thus, the receptive material is defined as one part of a specific binding pair and includes, but is not limited to, antigen/antibody, enzyme/substrate, oligonucleotide/DNA, chelator/metal, enzyme/inhibitor, bacteria/receptor, virus/receptor, hormone/receptor, DNA/RNA, or RNA/RNA, oligonucleotide/RNA, and binding of these species to any other species, as well as the interaction of these species with inorganic species.

The receptive material that is bound to the attachment layer is characterized by an ability to specifically bind the analyte or analytes of interest. The variety of materials that can be used as receptive material are limited only by the types of material which will combine selectively (with respect to any chosen sample) with a secondary partner. Subclasses of materials which can be included in the overall class of receptive materials includes toxins, antibodies, antigens, hormone receptors, parasites, cells, haptens, metabolizers, allergens, nucleic acids, nuclear materials, autoantibodies, blood proteins, cellular debris, enzymes, tissue proteins, enzyme substrates, coenzymes, neuron transmitters, viruses, viral particles, microorganisms, proteins, polysaccharides, chelators, drugs, and any other member of a specific binding pair. This list only incorporates some of the many different materials that can be coated onto the attachment layer to produce a thin film assay system. Whatever the selected analyte of interest is, the receptive material is designed to bind specifically with the analyte of interest.

The matrix containing the analyte of interest may be a fluid, a solid, a gas, or a bodily fluid such as mucous, saliva, urine, fecal material, tissue, marrow, cerebral spinal fluid, serum, plasma, whole blood, sputum, buffered solutions, extracted solutions, semen, vaginal secretions, pericardial, gastric, peritoneal, pleural, or other washes and the like. The analyte of interest may be an antigen, an antibody, an enzyme, a DNA fragment, an intact gene, a RNA fragment, a small molecule, a metal, a toxin, an environmental agent, a nucleic acid, a cytoplasm component, pili or flagella component, protein, polysaccharide, drug, or any other material, such as those listed in Table A. For example, receptive material for bacteria may specifically bind a surface membrane component, protein or lipid, a polysaccharide, a nucleic acid, or an enzyme. The analyte which is specific to the bacteria may be a polysaccharide, an enzyme, a nucleic acid, a membrane component, or an antibody produced by the host in response to the bacteria. The presence of the analyte may indicate an infectious disease (bacterial or viral), cancer or other metabolic disorder or condition. The presence of the analyte may be an indication of food poisoning or other toxic exposure. The analyte may indicate drug abuse or may monitor levels of therapeutic agents.

One of the most commonly encountered assay protocols for which this technology, can be utilized is an immunoassay. However, the general considerations apply to nucleic acid probes, enzyme/substrate, and other ligand/receptor assay formats. For immunoassays, an antibody may serve as the receptive material or it may be the analyte of interest. The receptive material, for example an antibody or an antigen, must form a stable, dense, reactive layer on the attachment layer of the test device. If an antigen is to be detected and an antibody is the receptive material, the antibody must be specific to the antigen of interest; and the antibody (receptive material) must bind the antigen (analyte) with sufficient avidity that the antigen is retained at the test surface. In some cases, the analyte may not simply bind the receptive material, but may cause a detectable modification of the receptive material to occur. This interaction could cause an increase in mass at the test surface or a decrease in the amount of receptive material on the test surface. An example of the latter is the interaction of a degradative enzyme or material with a specific, immobilized substrate. In this case, one would see a diffraction pattern before interaction with the analyte of interest, but the diffraction pattern would disappear if the analyte were present. The specific mechanism through which binding, hybridization, or interaction of the analyte with the receptive material occurs is not important to this invention, but may impact the reaction conditions used in the final assay protocol.

In general, the receptive material may be passively adhered to the attachment layer. If required, the free functional groups introduced onto the test surface by the attachment layer may be used for covalent attachment of receptive material to the test surface. Chemistries available for attachment of receptive materials are well known to those skilled in the art.

A wide range of techniques can be used to adhere the receptive material to the attachment layer. Test surfaces may be coated with receptive material by total immersion in a solution for a predetermined period of lime; application of solution in discrete arrays or patterns; spraying, ink jet, or other imprinting methods; or by spin coating from an appropriate solvent system. The technique selected should minimize the amount of receptive material required for coating a large number of test surfaces and maintain the stability/functionality of receptive material during application. The technique must also apply or adhere the receptive material to the attachment layer in a very uniform and reproducible fashion.

The receptor layer is formed from material selected from the group consisting of antigens, antibodies, oligonucleotides, chelators, enzymes, bacteria, bacterial pili, bacterial flagellar materials, nucleic acids, polysaccharides, lipids, proteins, carbohydrates, metals, viruses, hormones and receptors for said materials In the preferred embodiments, the biosensing device is configured and arranged to provide a pattern detectable by eye in response to transmission of polychromatic light when the analyte of interest is sandwiched between the receptive material and a secondary binding reagent.

The medium in which the analyte may reside can be solid,gel-like, liquid or gas. For purposes of detecting an analyte in a body fluid, the fluid is selected from the group consisting of urine, serum, plasma, spinal fluid, sputum, whole blood, saliva, uro-genital secretions, fecal extracts, pericardial, gastric, peritoneal, pleural washes, vaginal secretions, and a throat swab; and the method optionally includes using a spectrophotometer to measure the appearance of the refractive pattern. The most common gas that is contemplated as being used with the biosensing device of the present invention is air.

The biosensing device of the present invention utilizes methods of contact printing of patterned, self-assembling monolayers of alkanethiolates, carboxylic acids, hydroxamic acids, and phosphonic acids on metalized polymer films, desirably thermoplastic polymer films, the compositions produced thereby, and the use of these compositions. Patterned self-assembling monolayers allow for the controlled placement of fluids thereon which can contain a analyte receptor. The term "patterned self-assembling monolayers thereon" as used herein means the self-assembling monolayers in any pattern on the metalized polymer films including a solid pattern.

When the film with the self-assembling monolayers thereon is exposed to an analyte that is capable of reacting with the self-assembling monolayer, the film will produce optical diffraction patterns which differ depending on the reaction of the self-assembling monolayer with the analyte of interest. The liquid may be a high surface tension fluid such as water. The light can be in the visible spectrum, and be either reflected from the film, or transmitted through it, and the analyte can be any compound reacting with the self-assembling monolayer.

In preferred embodiments, the method involves contacting the substrate with a test sample potentially containing the analyte under conditions in which the substrate causes a change in the refractive index of the monolayer. When light is transmitted through the metalized thermoplastic polymer with the self-assembling monolayer, a visible pattern is formed and can be visualized by directing the light to a surface or by looking directly through the substrate.

In one embodiment, the present invention is contemplated in a dipstick form in which the micro-contact printed metalized film is mounted at the end of the dipstick. In use the dipstick is dipped into the liquid in which the suspected analyte may be present and allowed to remain for several minutes. The dipstick is then removed and then, either a light is projected through the metalized film or the film is observed with a light behind the film. If a pattern is observed, then the analyte is present in the liquid.

In another embodiment of the present invention, a multiple analyte test is constructed on the same support. As shown in FIG. 1, a strip 10 is provided with several micro-contact printed metalized films 20, 25, 30 and 35, each film having a self-assembled monolayer pattern 40 printed thereon. Each of the micro-contact printed metalized films 15, 20, 25, and 30 have a different receptive material that is different for different analytes. It can be seen that the present invention can be formatted in any array with a variety of micro-contact printed metalized films thereby allowing the user of the biosensor device of the present invention to detect the presence of multiple analytes in a medium using a single test.

In yet another embodiment of the present invention, the biosensor can be attached to an adhesively backed sticker or decal which can then be placed on a hard surface or container wall. The biosensor can be placed on the inside surface of a container such as a food package or a glass vial. The biosensor can then be visualized to determine whether there is microbial contamination.

Self-assembled monolayers on metalized film

Self-assembled monolayers of organic compounds on inorganic or metal surfaces are an important aspect of the present invention. Although there are many different systems of self-assembling monolayers based on different organic components and supports, desired systems are those of alkanethiolates, $HS(CH_2)_nR$, on gold films. Typically, a gold film, 5 to 2000 nm thick, is supported on a titanium-primed $Si/SiO_2$ wafer or glass sheet. The titanium serves as an adhesion promoter between gold and the support. The alkanethiols chemisorb on the gold surface from a solution in which the gold film is immersed, and form adsorbed alkanethiolates with loss of hydrogen. Adsorption can also occur from the vapor. Self-assembling monolayers formed on gold from long-chain alkanethiolates of structure $X(CH_2)_nY(CH_2)_mS$ are highly ordered and can be considered as crystalline or quasi-crystalline molecular arrays. A wide variety of organic functional groups (X,Y) can be incorporated into the surface or interior of the monolayer.

Self-assembling monolayers can therefore be tailored to provide a wide variety of material properties: wettability and protection against corrosion by chemical etchants are especially relevant to microcontact printing.

Figure 2:
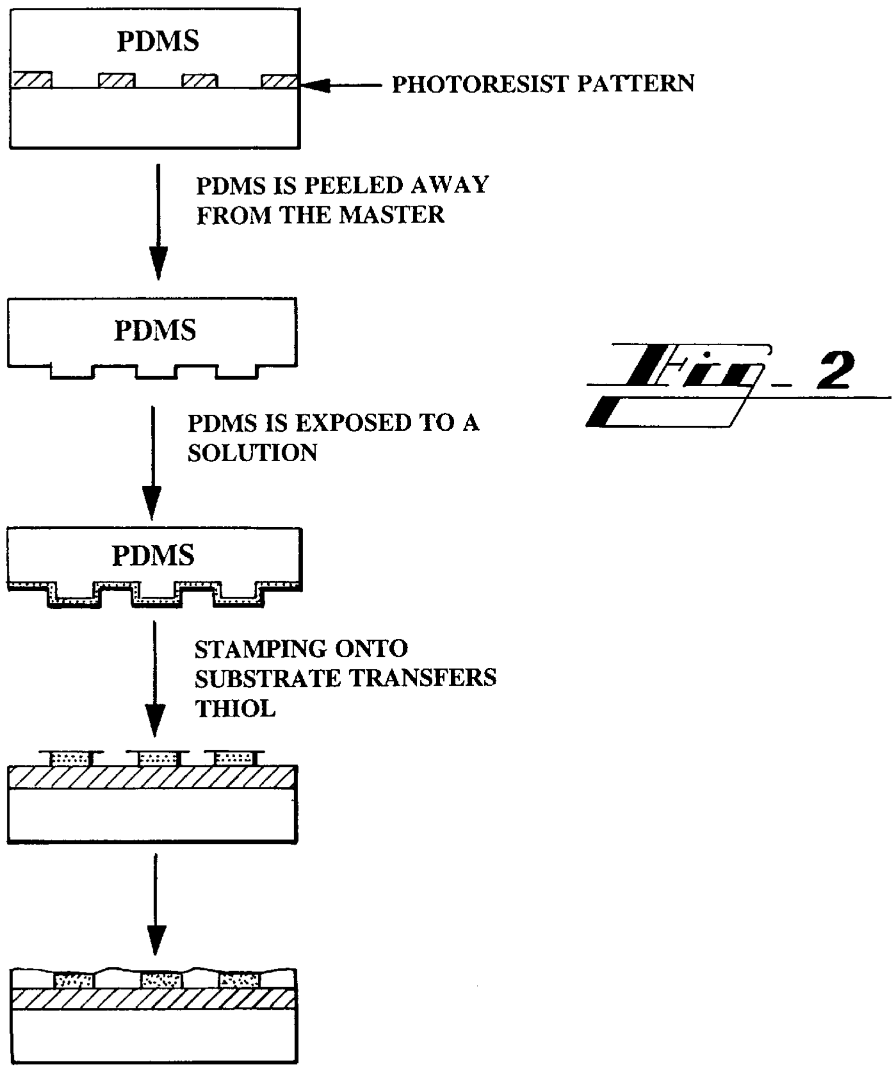
FIG. 2 is a schematic of contact printing of self-assembling monolayers. A polydimethylsiloxane (PDMS; silicone elastomer 184; Dow Corning Corp., Midland, Mich.) is polymerized on a silicone master containing a pre-determined pattern. This pattern has pixels approaching one micron in size, and could represent the diffraction image of a simple hologram. The PDMS is peeled away from the master, and then exposed to a solution containing $HS(CH_2)_{15}CH_3$. The alkane-thiol coated stamp is then stamped onto the gold-coated substrate. Then, the surface of the substrate is exposed to a solution containing a different alkane-thiol such as $HS(CH_2)_{11}OH$.

FIG. 2 outlines the procedure used for microcontact printing. An elastomeric stamp is used to transfer alkanethiol "ink" to a gold surface by contact; if the stamp is patterned, a patterned self-assembling monolayer forms. The stamp is fabricated by casting polydimethylsiloxane (PDMS) on a master having the desired pattern. Masters are prepared using standard photolithographic techniques, or constructed from existing materials having microscale surface features.

In a typical experimental procedure, a photolithographically produced master is placed in a glass or plastic Petri dish, and a 10:1 ratio (w:w or v:v) mixture or SYLGARD® silicone elastomer 184 and SYLGARD® silicone elastomer 184curing agent (Dow Corning Corporation) is poured over it. The elastomer is allowed to sit for approximately 30 minutes at room temperature and reduced pressure to degas, then cured for 1–2 hours at 60° C., and gently peeled from the master. "Inking" of the elastomeric stamp is accomplished by exposing the stamp to a 0.1 to 1.0 mM solution of alkanethiol in anhydrous ethanol, either by pouring the solution over the surface of the stamp, or by rubbing the stamp gently with a Q-TIP® that has been saturated with the inking solution. The stamp is allowed to dry until no liquid is visible by eye on the surface of the stamp (typically about 60 seconds), either under ambient conditions, or by exposure to a stream of nitrogen gas. Following inking, the stamp is applied (typically by hand) to a gold surface. Very light hand pressure is used to aid in complete contact between the stamp and the surface. The stamp is then gently peeled from the surface. Following removal of the stamp, the surface is washed of excess thiol and the patterned gold surface can be subjected to chemical etchants (see below) that selectively remove underivatized areas of the gold surface, and if desired, the underlying support(s). Alternatively, further derivatization of unstamped areas can be accomplished, either by using a second stamp, or by washing the entire surface with a different alkanethiol.

The elastomeric character of the stamp is important to the success of the process. Polydimethylsiloxane (PDMS), when cured, is sufficiently elastomeric to allow good conformal contact of the stamp and the surface, even for surfaces with significant relief; this contact is essential for efficient contact transfer of the alkanethiol "ink" to the gold film. The elastomeric properties of PDMS are also important when the stamp is removed from the master: if the stamp were rigid (as is the master) it would be difficult to separate the stamp and master after curing without damaging one of the two substrates. PDMS is also sufficiently rigid to retain its shape, even for features with sub-micron dimensions: we have successfully generated patterns with lines as small as 200 nm in width. The surface of PDMS has a low interfacial free energy (y=22.1 dynes/cm), and the stamp does not adhere to the gold film. The stamp is durable in that the same stamp can be used up to 100 times over a period of several months without significant degradation in performance. The polymeric nature of PDMS also plays a critical role in the inking procedure, by enabling the stamp to absorb the alkanethiol ink by swelling. Produce printing roll for stamp to allow for a continuous printing operation.

Microcontact printing on gold surfaces can be conducted with a variety of alkanethiol "inks". Alkanethiols that do not undergo reactive spreading (after application to the gold film) are required for formation of small features with high resolution. For stamping in air, one can use autophobic alkanethiols such as hexadecanethiol. Microcontact printing of other non-autophobic alkanethiols, for example, $HS(CH_2)_{15}COOH$, can be conducted by stamping under a liquid such as water. Patterned self-assembling monolayers of alkanethiols on gold provide excellent resist character with a number of wet-chemical etchants.

In one embodiment of the present invention, the self-assembling monolayer is formed of a carboxy-terminated alkane thiol stamped with a patterned elastomeric stamp onto a gold-surfaced thermoplastic film such as MYLAR®. The alkanethiol is inked with a solution of alkanethiol in ethanol, dried, and brought into contact with a surface of gold. The alkanethiol is transferred to the surface only at those regions where the stamp contacts the surface, producing a pattern of self-assembling monolayer which is defined by the pattern of the stamp. Optionally, areas of unmodified gold surface next to the stamped areas can be rendered hydrophobic by reaction with a methyl-terminated alkane thiol.

A more detailed description of the methods and compositions of the present invention follows. All publications cited herein are incorporated by reference in their entirety.

Any thermoplastic film upon which a metal substrate can be deposited is suitable for the present invention. These include, but are not limited to polymers such as: polyethylene-terephthalate (MYLAR®), acrylonitrile-butadiene-styrene, acrylonitrile-methyl acrylate copolymer, cellophane, cellulosic polymers such as ethyl cellulose, cellulose acetate, cellulose acetate butyrate, cellulose propionate, cellulose triacetate, cellulose triacetate, polyethylene, polyethylene-vinyl acetate copolymers, ionomers (ethylene polymers) polyethylene-nylon copolymers, polypropylene, methyl pentene polymers, polyvinyl fluoride, and aromatic polysulfones. Preferably, the plastic film has an optical transparency of greater than 80%. Other suitable thermoplastics and suppliers may be found, for example, in reference works such as the *Modern Plastics Encyclopedia* (McGraw-Hill Publishing Co., New York 1923–1996).

In one embodiment of the invention, the thermoplastic film with the metal coating thereon has an optical transparency of between approximately 5% and 95%. A more desired optical transparency for the thermoplastic film used in the present invention is between approximately 20% and 80%. In a desired embodiment of the present invention, the thermoplastic film has at least an approximately 80% optical transparency, and the thickness of the metal coating is such as to maintain an optical transparency greater than about 20%, so that diffraction patterns can be produced by either reflected or transmitted light. This corresponds to a metal coating thickness of about 20 nm. However, in other embodiments of the invention, the gold thickness may be between approximately 1 nm and 1000 nm.

The preferred metal for deposition on the film is gold. However, silver, aluminum, chromium, copper, iron, zirconium, platinum and nickel, as well as oxides of these metals, may be used. Chromium oxide and gold oxide can be used to make self-assembling monolayers.

In principle, any surface with corrugations of appropriate size could be used as masters. The process of microcontact printing starts with an appropriate relief structure, from which an elastomeric stamp is cast. This 'master' template may be generated photolithographically, or by other procedures, such as commercially available diffraction gratings. In one embodiment, the stamp may be made from polydimethylsiloxane.

In another embodiment, the invention features an optical assay device, having an optically active receptive surface configured and arranged to allow simultaneous assay of a plurality of samples on the surface for one analyte of interest, and an automated liquid handling apparatus (e.g., a pipetting device) configured and arranged to dispense sample and reagent solutions to the surface.

Below is provided an indication of the methodology by which the optimal materials and methods useful for construction of optical test surfaces of this invention can be made. Generally, the present invention includes novel optically active test surfaces for the direct detection of an analyte. These test surfaces have a specific receptive material bound to the test surface by use of an attachment layer. Thus, the present invention provides a detection method which includes selecting an optical substrate, attaching receptive material specific to the analyte of interest on the upper layer of the substrate, contacting the receptive material with a sample fluid containing the analyte of interest, and then examining the change in diffraction of transmitted light produced at the coated surface by observing whether a diffraction pattern is formed.

The present invention has a broad range of applications and, may be utilized in a variety of specific binding pair assay methods. For example, the devices of this invention can be used in immunoassay methods for either antigen or antibody detection. The devices may be adapted for use in direct, indirect, or competitive detection schemes, for determination of enzymatic activity, and for detection of small organic molecules (e.g., drugs of abuse, therapeutic drugs, environmental agents), as well as detection of nucleic acids.

In one embodiment of the present invention, the self-assembling monolayer has the following general formula:

X—R—Y

X is reactive with metal or metal oxide. For example, X may be asymmetrical or symmetrical disulfide (—R'SSY', —RSSY), sulfide (—R'SY', —RSY), diselenide (—R'Se—SeY'), selenide (—R'SeY', —RSeY), thiol (—SH), nitrile (—CN), isonitrile, nitro (—$NO_2$), selenol (—SeH), trivalent phosphorous compounds, isothiocyanate, xanthate, thiocarbamate, phosphine, thioacid or dithioacid, carboxylic acids, hydroxylic acids, and hydroxamic acids.

R and R' are hydrocarbon chains which may optionally be interrupted by hetero atoms and which are preferably non-branched for the sake of optimum dense packing. At room temperature, R is greater than or equal to seven carbon atoms in length, in order to overcome natural randomizing of the self-assembling monolayer. At colder temperatures, R may be shorter. In one embodiment, R is —$(CH_2)_n$— where n is between 10 and 12, inclusive. The carbon chain may optionally be perfluorinated. It is to be understood that the carbon chain may be any length.

Y and Y' may have any surface property of interest. For example, Y and Y' could be any among the great number of groups used for immobilization in liquid chromatography techniques, such as hydroxy, carboxyl, amino, aldehyde, hydrazide, carbonyl, epoxy, or vinyl groups. Examples of sensing layer materials are set forth in "Patterning Self-Assembled Monolayers Using Microcontact Printing: A New Technology for Biosensors?," by Milan Mrksich and George M. Whitesides, published in TIBTECH, June, 1995 (Vol. 13), pp. 228–235, hereby incorporated by reference.

Self assembling monolayers of alkyl phosphonic, hydroxamic, and carboxylic acids may also be useful for the methods and compositions of the present invention. Since alkanethiols do not adsorb to the surfaces of many metal oxides, carboxylic acids, phosphonic acids, and hydroxamic acids may be preferred for X for those metal oxides. See J. P. Folkers, G. M. Whitesides, et al., *Langmuir,* 1995, vol. 11, pp. 813–824.

R may also be of the form $(CH_2)_a$—Z—$(CH_2)_b$, where $a \geqq 0$, $B \geqq 7$, and Z is any chemical functionality of interest, such as sulfones, urea, lactam, etc.

The stamp may be applied in air, or under a fluid such as water to prevent excess diffusion of the alkanethiol. For large-scale or continuous printing processes, it is most desirable to print in air, since shorter contact times are desirable for those processes.

In one embodiment of the present invention, the pattern is formed on the metalized thermoplastic polymer with the self-assembling monolayer. In another embodiment of the present invention, the relief of the pattern is formed with the self-assembling monolayer. After the stamping process, the metalized areas on the plastic may optionally be passivated, for example, with a methyl-terminated self-assembling monolayer such as hexadecylmercaptan.

This invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

EXAMPLE 1

Printing of gold-coated MYLAR® (polyethylene terephthalate) with patterns of 16-mercaptohexadecanoic acid and hexadecanethiol Patterns of gold-coated MYLAR® (polyethylene terephthalate) are printed with patterns of 16 mercaptohexadecanoic acid and hexadecanethiol, as shown in FIG. 2, and described below.

Figure 3:
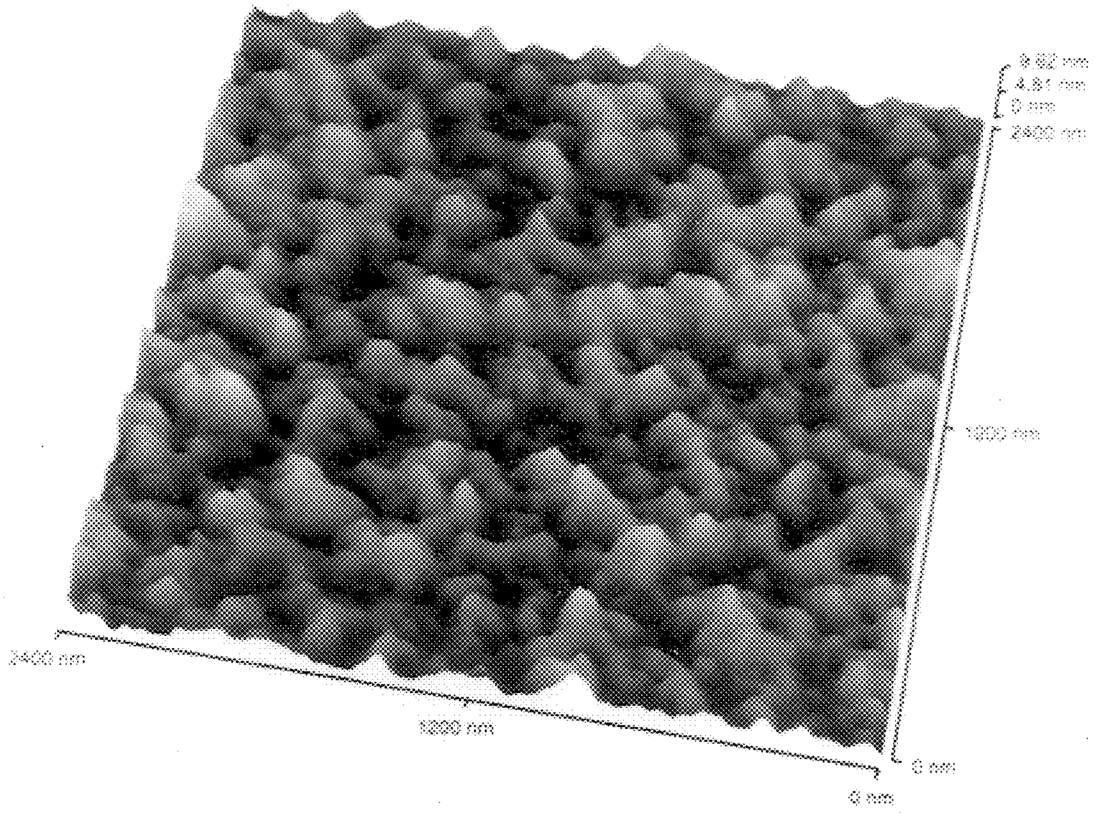
FIG. 3 is an atomic force microscopy image of evaporated gold on MYLAR®, purchased from Courtaulds Performance Films (Canoga Park, Calif.). The average roughness of the gold layer is 3–4 nanometers, with maximum roughness of 9 nanometers.
Figure 5:
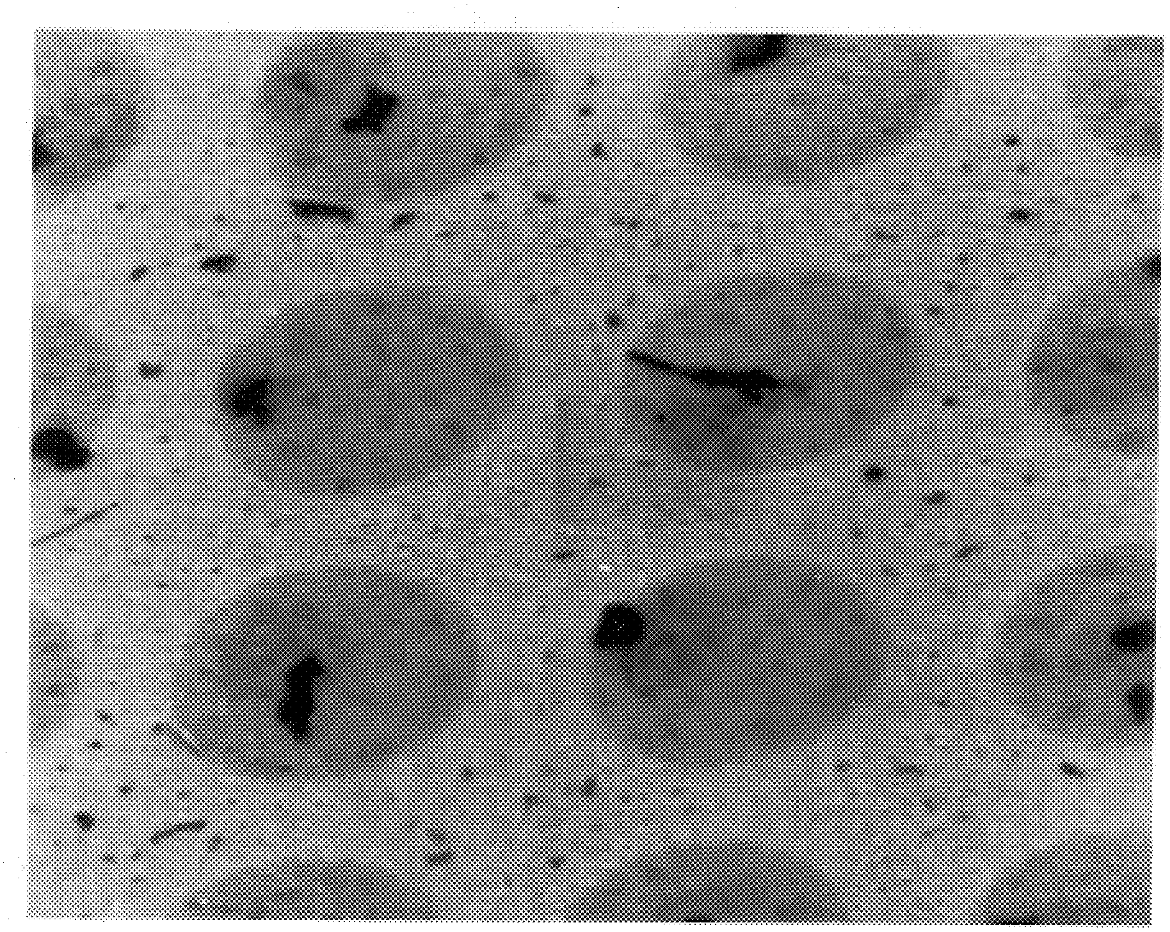
FIG. 5 is a field emission secondary electron microscope image of 10 micron-diameter circles of hydrophilic self-assembling monolayers formed by printing of 16-mercaptohexadecanoic acid, as described in Example 1, below.

MYLAR® film modified with a plasma deposited gold topcoat is obtained from Courtaulds Performance Films (Canoga Park, Calif. 91304). An atomic force microscopy image of this MYLAR® film is shown in FIG. 3. Polymer film thickness between 2 and 7 mils and gold topcoats producing a surface resistance of 65 ohms per square centimeter with a visible light transmittance between 20% and 65% are used.

Patterns of hydrophilic, carboxy-terminated alkane thiols are stamped onto gold-coated film using 16 mercaptohexadecanoic acid by the following method. An exposed and developed photoresist pattern of 10 micron diameter circles on a silicon wafer is used as the master. Patterns have features that are defined by spacing the features approximately less than 10 microns apart, and most desirably less than 1–5 microns apart. Polydimethylsiloxane (PDMS; silicone elastomer 184; Dow Corning Co., Midland, Mich.), is polymerized on a master to produce a stamp with ten micron-diameter circles spaced five microns apart. The stamp is inked by exposure to a solution (1 to 10 mM in ethanol) of 16-mercaptohexadecanoic acid, and allowed to air-dry. The substrate is contacted with the stamp for 50 seconds and washed for 2 to 4 seconds with a solution of hexadecanethiol (1 to 10 mM in ethanol). The substrate is finally washed for 10 seconds in ethanol and dried in a stream of nitrogen. The results of this printing are shown in FIGS. 4*a* through *c* and FIG. 5 for the 10 micron diameter circles of the carboxylic acid terminated self-assembling monolayer.

These hydrophilic self-assembling monolayer circles allow for selective placement of high surface tension fluids such as water, triethylene glycol, or ultraviolet light curable urethane acrylic adhesives. These liquids can contain dissolved and suspended reagents that react chemically or physically with targeted analytes, thus making the coated plastic film a collection of 10 micron microreactors suitable for low cost, disposable chemical sensors. An example of such a device is shown in FIG. 6*a* and 6*b*, FIG. 7, and FIG. 8*a* and 8*b*.

Diffraction of visible light is shown with these compositions. Both reflected and transmitted diffraction patterns are observed when using 5 mW, 670 nM laser illumination. FIG. 6*b* is a photograph of the diffraction pattern formed by visible light shown through the self-assembling monolayer pattern of FIG. 6*a*. Rainbow diffraction colors are observed with transmitted white light.

EXAMPLE 2

Experimental procedure for detecting *Saccharomyces cerevisae* using a hexamer sugar thiostructure. The metalized MYLAR® film is cleaned for 20 minutes with piranha solution. The film is then rinsed with millipore purified water until the wash water is neutral. The surface is then cleaned using UV-ozone cleaning for 30 minutes. The $CH_3(CH_2)_{15}$—SH (1 mM in EtOH), is applied on the stamp surface with a Q-TIP®. The stamp is then pressed on the gold surface of the MYLAR® film for 20 seconds. The imprint forms an inverse circle structure. The printed film is rinsed with EtOH and dried under nitrogen.

The non-stamped surface is coated with the hexamer sugar thiol by dropping 40 μL of a 0.5 mM saccharide solution onto the surface. After 20 seconds, the surplus of the saccharide thiol solution is rinsed off. This wafer is suspended upside down into a yeast suspension of 5 g of yeast in 30 ml of isotonic NaCl solution. After 40 minutes, the surface is washed with EtOH. The diffraction pattern are generated by using a He/Ne laser beam (lambda=832.8 nm).

EXAMPLE 3

Figure 9A:
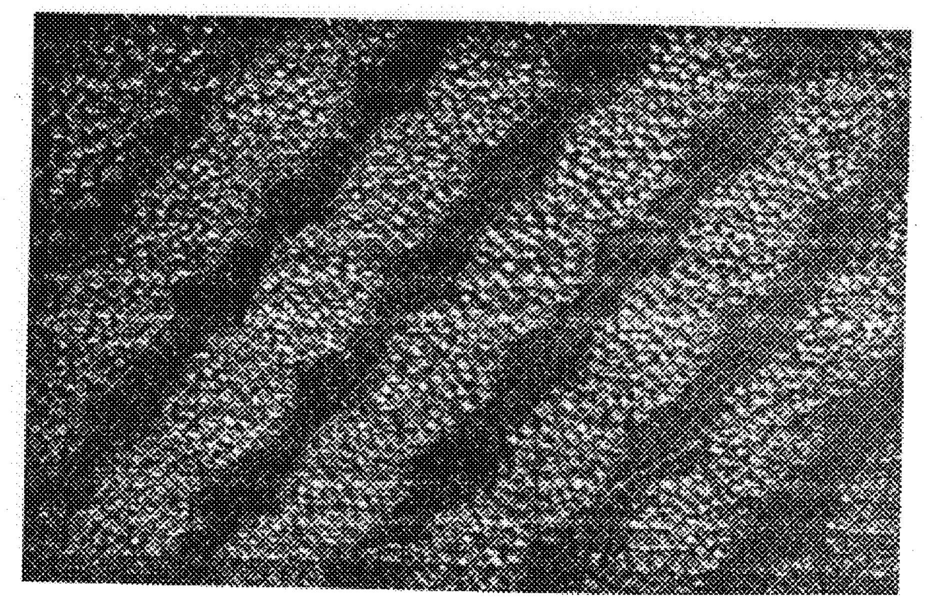
FIGS. 9*a* and 9*b* are diffraction biosensors for *Saccharomyces cerevasiae* based on contact printing of self-assembling monolayers.
Figure 9B:
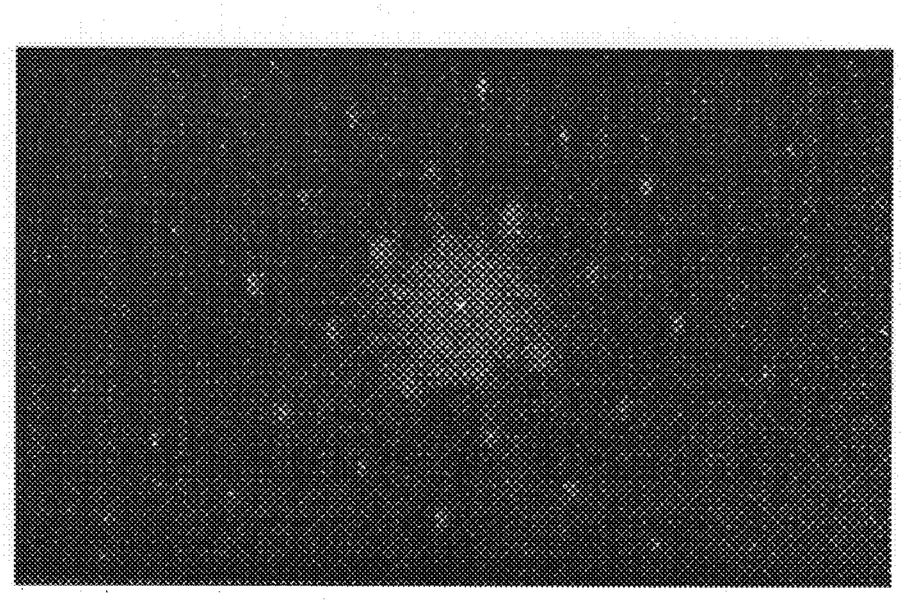

Patterns of a hydrophilic self-assembling monolayers with oligomers of an average of six glucose molecules attached at the end of the alkane thiol are produced on metalized MYLAR®. (See Example 2) The 10 micron diameter circles spaced five microns apart are used to generate the plate upon which the target organism would attach. The non-stamped area is rendered hydrophobic via reaction with a methyl terminated alkane thiol. This sample is non-diffracting as produced. A one square cm piece of this sample is exposed for 40 minutes to 30 mL of an aqueous solution containing 1 gram of bakers yeast and 0.9 wt % saline, followed by washing with copious amounts of water. The photomicrograph of the sample and the diffraction image produced from the sample irradiated with a He—Ne laser are shown in FIG. 9*a* and 9*b*, respectively. A control sample not containing the sugar shows no diffraction and no attachment of particles. As seen in FIG. 9*a*, yeast has attached to the 10 micron circles of the sugar thiol, but have not attached to the hydrophobic, methyl terminated self-assembling monolayers. Some coalescence of the circles with attached yeast in one preferred direction is evident. FIG. 9*b* reveals that diffraction of 632 nM radiation results with yeast attachment. Diffraction serves as the basis of sensing the presence of yeast cells.

EXAMPLE 4

Detection of Saccharomyces cerevisae

The metalized MYLAR® film that is to be printed is cleaned for 20 minutes with piranha solution, The film is rinsed with millipore purified water until neutralization and then UV-ozone cleaned for 30 minutes. Microcontact printing of the hydrophobic layer, $CH_3(CH_2)_{15}$—SH (1 mm in EtOH), is applied on the stamp surface with a Q-TIP®. The stamp is pressed on the gold surface of the MYLAR® film for 20 seconds. The imprint forms an inverse circle structure. The printed film is rinsed with EtOH and dried under nitrogen.

The non-stamped surface is coated with the hexamer sugar thiol by dropping 40 μL of a 0.5 mM saccharide solution onto the surface. After 20 seconds, the surplus of the saccharide thiol solution is rinsed off. This wafer is suspended upside down into a yeast suspension of 5 g of yeast in 30 ml of isotonic NaCl solution. After 40 minutes, the surface is washed with EtOH. The diffraction pattern are generated by using a He/Ne laser beam (lambda=832.8 nm)

EXAMPLE 5

Biosensors specific for *Candida tropicalis*

Agar plates (universal medium for yeast) are inoculated with a clone of original *Candida tropicalis* (DSM 1348). After 2 days at 25° C., the cells are harvested and diluted with the yeast medium. The suspension is then treated in an ultrasonic bath to separate the cell aggregates.

The experimental procedure of micro contact printing is the same as in Example 2. The thiols used in this experiment are HS-$(CH_2)_{15}$-$CH_3$-designated $CH_3$HS-$(CH_2)_{15}$COOH,-designated COOH The incubation time of the gold-water in cell solution ranged between 1 night and 3 days. The samples are not rinsed off after the incubation. Following combinations are represented in designated figures.

Figure 10A:
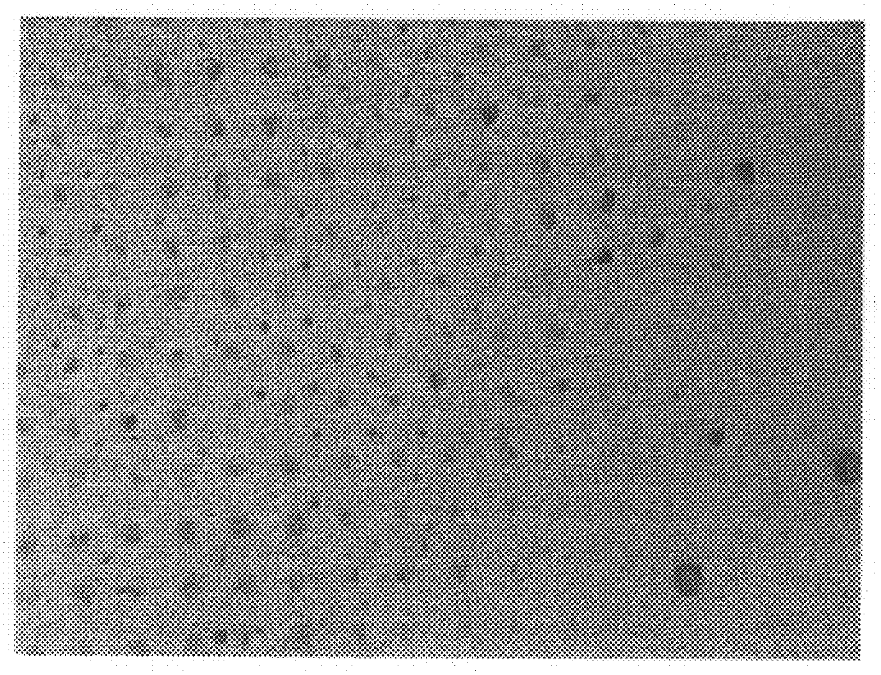
FIG. 10 shows the adherence of *Candida tropicalis* as a function of surface modification. In this figure the circles are $HS—(CH_2)_{15}—CH_3$—designated $CH_3$and the surrounding area is $HS—(CH_2)_{15}COOH$ designated COOH.
Figure 10B:
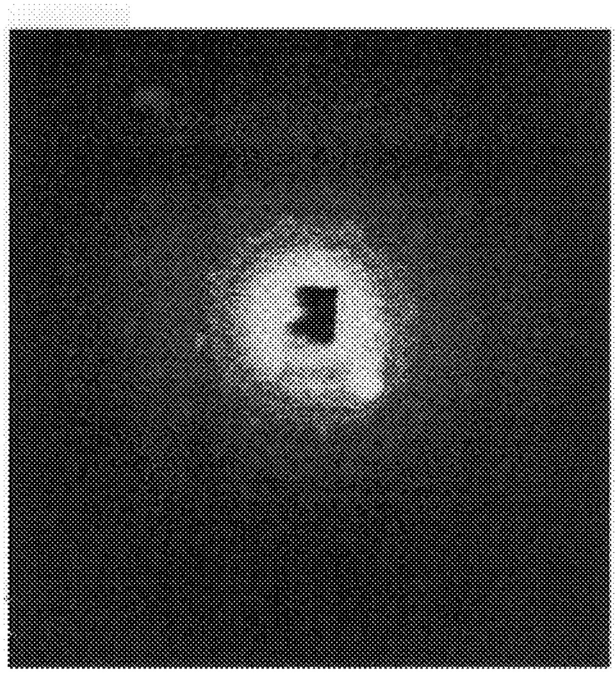

3) circle is $CH_3$-surrounding area is COOH incubated overnight (FIG. 10)

Figure 11A:
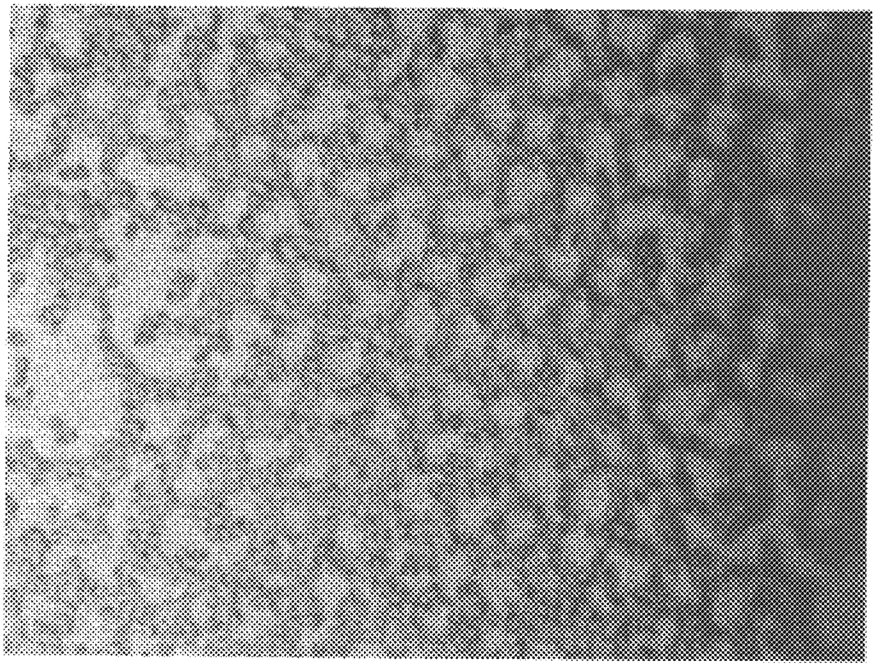
FIG. 11 shows the adherence of *Candida tropicalis* as a function of surface modification. In this figure the circles are $HS—(CH_2)_{15}COOH$ designated COOH and the surrounding area is $HS—(CH_2)_{15}—CH_3$designated $CH_3$.
Figure 11B:
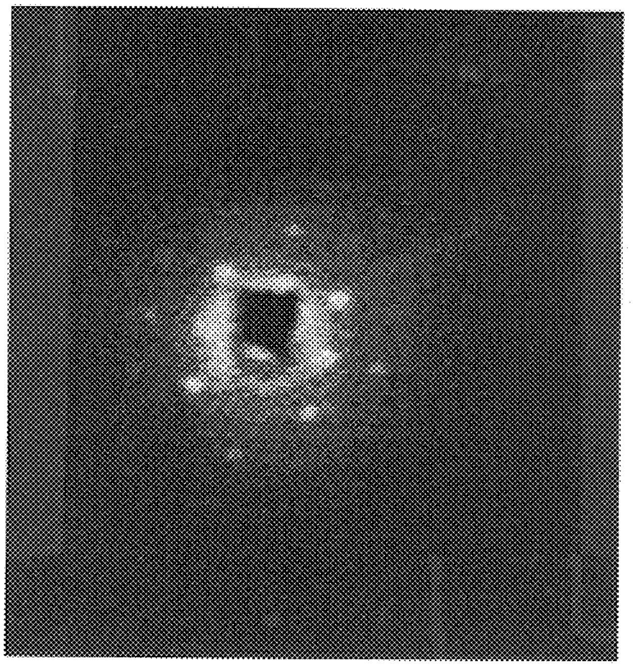

2) circle is COOH-surrounding area is $CH_3$-incubated overnight (FIG. 11)

EXAMPLE 6

A gold/MYLAR substrate is contact printed using a stamp of 10μ circles coated with an ethanolic solution of mercaptohexadecanoic acid. The surrounding areas of the circles are then filled in with an ethanol solution of hexadecane thiol. The acid end groups are esterified with L-fucose using carbodiimide coupling. The procedure involved placing the contact printed gold/MYLAR® in a 41 mM dicyclohexyl carbodiimide (DCC) solution in pyridine for 5–6 minutes, then immediately transferring to a vial containing 3.3 mM pyridine solution of L-fucose. After 2½ hours, the gold/MYLAR® sample is removed thoroughly rinsed with distilled water then ethanol and dried.

Figure 12:
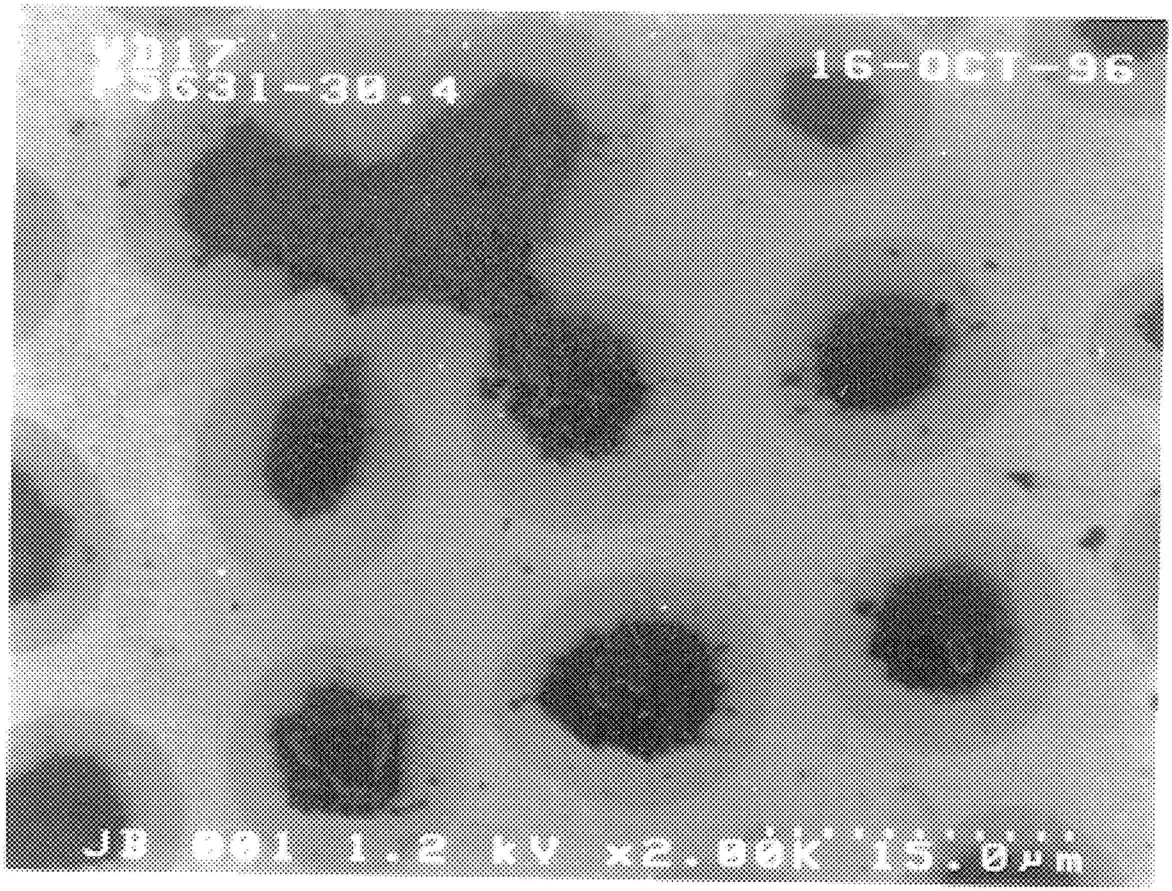
FIG. 12 shows a *Saccharomyces cerevasiae* cell undergoing mitosis.
Figure 13:
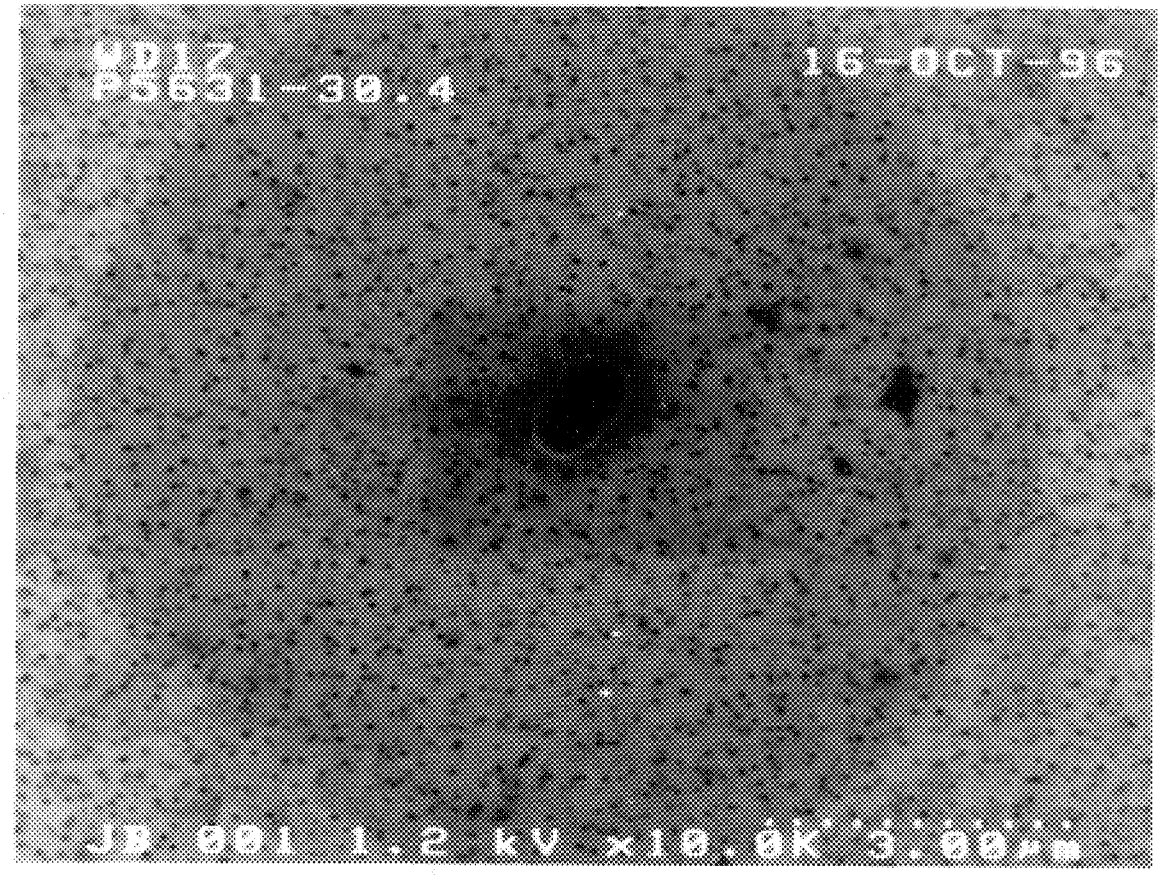
FIG. 13 shows *Saccharomyces cerevasiae* on 10$\mu$ circles with L-fucose endgroup.

This sample is exposed to a suspension of 0.5 g baker's yeast (*Saccharomyces cerevasiae*) in 15 ml 0.9% aqueous sodium chloride solution. After 8 days, the sample is briefly rinsed with distilled water and dried in a nitrogen stream. The sample diffracted light when irradiated with a He/Ne laser beam (lambda=832.8 nm), and scanning electron microscopy (SEM) revealed the presence of the yeast organisms in the 10 micron circles. (See FIG. 13). FIG. 12 shows a yeast cell undergoing mitosis. FIG. 13 demonstrates that the yeast cells are still viable, even after binding to the circles.

EXAMPLE 7

A gold/MYLAR® substrate is contact printed using a stamp of 10 micron circles coated with an ethanolic solution of mercaptohexadecanoic acid. The surrounding areas of the circles are then filled in with an ethanolic solution of hexadecane thiol.

Figure 14A:
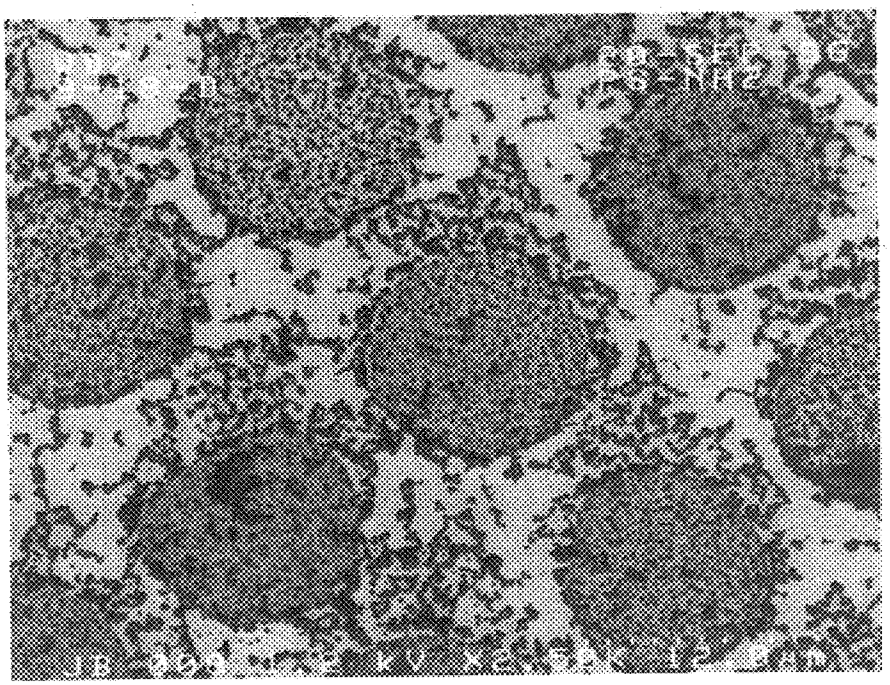
FIG. 14 shows the binding of amino modified polystyrene particles to circles coated with mercaptohexadecanoic acid.
Figure 14B:
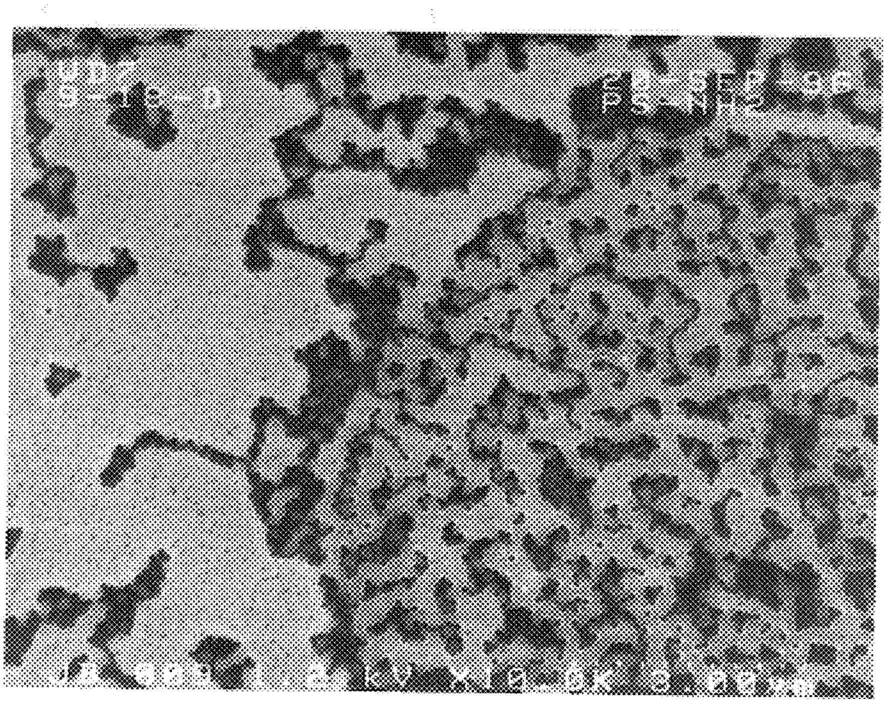

This sample is then exposed to an aqueous suspension of approximately $10^{10}$ particles/ml of 131 nm amino modified polystyrene particles (Catalog #F103092 from Seradyn). After two days, the sample is removed and gently rinsed with ethanol to remove unbound particles. A portion of the sample diffracted light from a laser, SEM analysis showed that the particles tended to aggregate around the circles. (See FIG. 14).

EXAMPLE 8

A gold/silicon substrate is contact printed using a stamp of 10 micron circles coated with an ethanolic solution of mercaptohexadecanoic acid. The acid end groups are esterified with D-mannose using carbodiimide coupling. The procedure involved placing the contact printing gold/silicon in an aqueous 41 mM solution of 1-ethyl-3-(3-dimethylaminopropyl) carbodiimide ("FDAC") for 5 to 8 minutes, then immediately transferring to a vial containing 9.9 mM aqueous solution of D-mannose. After 3½ hours, the gold/silicon sample is removed, thoroughly rinsed with distilled water, then with ethanol, and then dried.

Figure 15A:
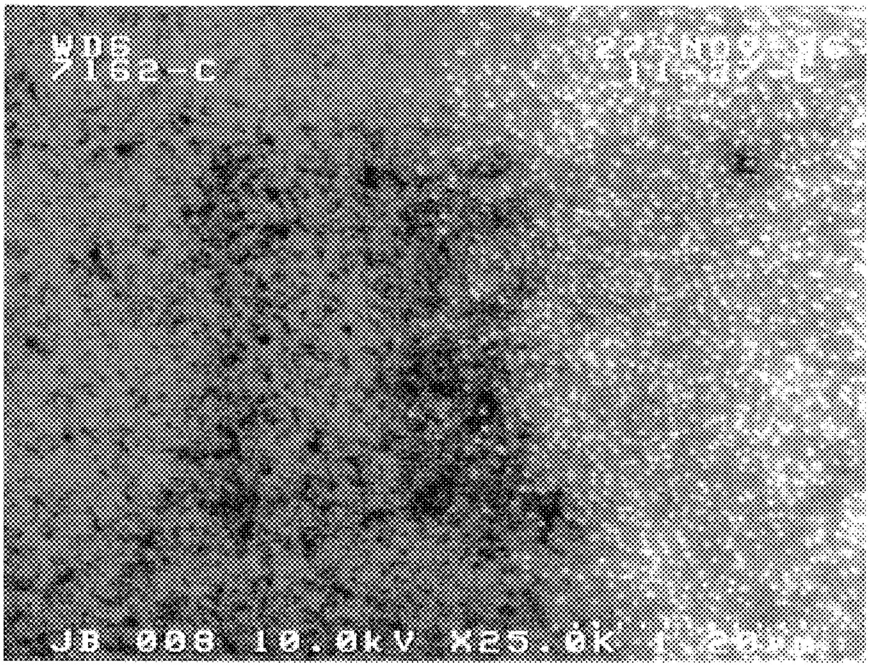
FIG. 15 shows a field emission secondary electron micrograph image of Concanavalin A labeled with 20 $\mu$m gold particles attached to a sugar modified, self-assembling monolayer. The 20 $\mu$m gold on the Concanavalin A produces high contrast for imaging.
Figure 15B:
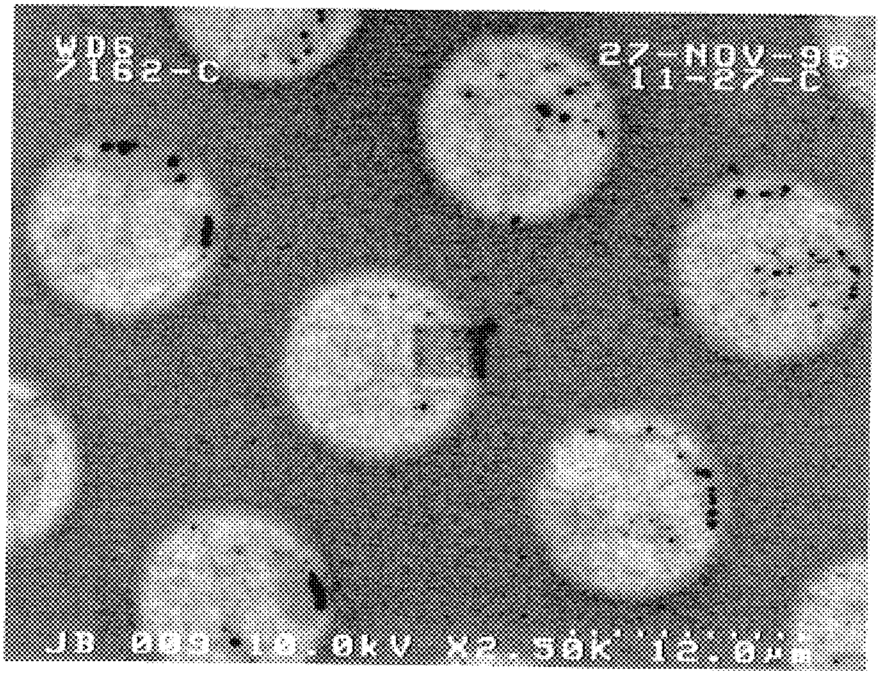

This sample is covered with a few drops of phosphate-buffered saline (20 mM phosphate, 80 mM sodium chloride, pH 7.4), then 20 μL of Concanavalin A labeled with 20 nm Gold colloid (Sigma Chemical Company, St. Louis, Mo.) is added to the buffer drop. After 30 minutes, the sample is thoroughly rinsed in the buffer solution, followed by more rinses with distilled water, and then dried under a nitrogen stream. SEM analysis shows the presence of 20 nm sized gold particles bound to the circles (See FIG. 15). Because Concanavalin A is specific for binding to mannose, this test confirms the presence of mannose in the 10 micron circles.

Those skilled in the art will now see that certain modifications can be made to the invention herein disclosed with respect to the illustrated embodiments, without departing from the spirit of the instant invention. And while the invention has been described above with respect to the preferred embodiments, it will be understood that the invention is adapted to numerous rearrangements, modifications, and alterations, all such arrangements, modifications, and alterations are intended to be within the scope of the appended claims.

We claim:

1. A biosensor comprising:

a polymer film coated with metal; and a self-assembling monolayer printed onto the polymer film wherein the self-assembling monolayer has a receptive material thereon that is specific for an analyte;

wherein the self-assembling monolayer is printed in a first, non-diffracting pattern such that when the biosensor binds an analyte, the biosensor diffracts transmitted light to form a second pattern, wherein the second pattern is a diffraction pattern; and further wherein the analyte has a size of the same order as the wavelength of the transmitted light thereby resulting in the diffraction of the transmitted light.

2. The biosensor of claim 1, wherein the diffraction pattern in visible.

3. The biosensor of claim 1, wherein the metal is selected from the group consisting of gold, silver, chromium, nickel, platinum, aluminum, iron, copper, gold oxide, chromium oxide or zirconium.

4. The biosensor of claim 1, wherein the metal is gold.

5. The biosensor of claim 4, wherein the gold coating is between approximately 1 nanometer and 1000 nanometers in thickness.

6. The biosensor of claim 1, wherein the polymer film is polyethylene-terephthalate, acrylonitrile-butadiene-styrene, acrylonitrile-methyl acrylate copolymer, cellophane, cellulosic polymers such as ethyl cellulose, cellulose acetate, cellulose acetate butyrate, cellulose propionate, cellulose triacetate, cellulose triacetate, polyethylene, polyethylene-vinyl acetate copolymers, ionomers (ethylene polymers) polyethylene-nylon copolymers, polypropylene, methyl pentene polymers, polyvinyl fluoride, and aromatic polysulfones.

7. The biosensor of claim 6, wherein the polymer film is polyethylene-terephthalate.

8. The biosensor of claim 1, wherein the thermoplastic film is optically transparent.

9. The biosensor of claim 1, wherein the thermoplastic film has an optical transparency between 5% and 95%.

10. The biosensor of claim 1, wherein the thermoplastic film has an optical transparency between approximately 20% and 80%.

11. The biosensor of claim 1, wherein the self-assembling monolayer is formed from compounds with the following general formula:

X—R—Y wherein:

X is reactive with the metal or metal oxide on the polymer film;

R is a hydrocarbon chain; and

Y is a compound with any property of interest.

12. The biosensor of claim 11, wherein:

X is a asymmetrical or symmetrical disulfide (—SSY', —SSY), sulfide (—'SY', SY), diselenide (—'Se—

SeY'), selenide (SeY', —SeY), thiol (—SH), nitrile (—CN), isonitrile, nitro (—$NO_2$), selenol (—SeH), trivalent phosphorous compounds, isothiocyanate, xanthate, thiocarbamate, phosphine, thioacid or dithioacid, carboxylic acids, hydroxylic acids, and hydroxamic acids;

R and R' are hydrocarbon chains which may optionally be interrupted by hetero atoms, and which may optionally be perfluorinated, and which are preferably non-branched; and Y and Y' are hydroxy, carboxyl, amino, aldehyde, hydrazide, carbonyl, epoxy, or vinyl groups.

13. The biosensor of claim 11, wherein R is greater than 7 carbon atoms in length.

14. The biosensor of claim 11, wherein R is a compound of the form $(CH_2)_a$—Z—$(CH_2)_b$, wherein a≧0, b≧7, and Z is any chemical functionality of interest.

15. The biosensor of claim 14, wherein Z is selected from the group consisting of sulfones, lactams, and urea.

16. The biosensor of claim 1, wherein there are two or more self-assembling monolayers with different chemical properties.

17. The biosensor of claim 1, wherein a first self-assembling monolayer is hydrophobic, and a second self-assembling monolayer is hydrophilic.

18. The biosensor of claim 1, wherein the analyte is bacteria, yeast, fungus, virus, rheumatoid factor, IgG, IgM, IgA and IgE antibodies, carcinoembryonic antigen, streptococcus Group A antigen, viral antigens, antigens associated with autoimmune disease, allergens, tumor antigens, streptococcus Group B antigen, HIV I or HIV II antigen, antibodies viruses, antigens specific to RSV, an antibody, antigen, enzyme, hormone, polysaccharide, protein, lipid, carbohydrate, drug or nucleic acid, *Neisseria meningitides* groups A, B, C, Y and W sub 135, *Streptococcus pneumoniae, E. coli* K1, *Haemophilus influenza* type B, an antigen derived from microorganisms, a hapten, a drug of abuse, a therapeutic drug, an environmental agents, or antigens specific to Hepatitis.

19. The biosensor of claim 18, wherein the analyte is bacteria, yeast, fungus or virus.

20. The biosensor of claim 1, wherein the receptive material are antigens, antibodies, oligonucleotides, chelators, enzymes, bacteria, yeasts, fungi, viruses, bacterial pili, bacterial flagellar materials, nucleic acids, polysaccharides, lipids, proteins, carbohydrates, metals, hormones and receptors for said materials.

21. The biosensor of claim 19, wherein the fungus is Candida species.

22. The biosensor of claim 19, wherein the bacteria is Salmonella species.

23. The biosensor of claim 1, wherein the biosensor is attached to the inside wall of a container.

24. The biosensor of claim 23 wherein the container is a vial.

25. The biosensor of claim 23 wherein the container is a water bottle.

26. The biosensor of claim 23, wherein the container is a food container.

27. The biosensor of claim 1, wherein the biosensor is attached to the inside wall of a garment.

28. The biosensor of claim 26, wherein the garment is a diaper.

29. A method of making a biosensor comprising printing a pattern of self-assembling monolayers with a receptive material on a polymer film coated with metal, wherein the self-assembling monolayer is printed in a pattern such that when the biosensor binds an analyte, the biosensor diffracts transmitted light to form a diffraction pattern.

30. A method of making a biosensor comprising printing a pattern of self-assembling monolayers with a receptive material on a polymer film coated with metal;

wherein the self-assembling monolayer is printed in a first, non-diffracting pattern such that when the biosensor binds an analyte, the biosensor diffracts transmitted light to form a second pattern, wherein the second pattern is a diffraction pattern; and further wherein the analyte has a size of the same order as the wavelength of the transmitted light thereby resulting in the diffraction of the transmitted light.

31. The method of claim 29, wherein the metal is gold.

32. The method of claim 31, wherein the gold coating is between approximately 1 nanometer and 1000 nanometers in thickness.

33. The method of claim 28, wherein the polymer film is polyethylene-terephthalate, acrylonitrile-butadiene-styrene, acrylonitrile-methyl acrylate copolymer, cellophane, cellulosic polymers such as ethyl cellulose, cellulose acetate, cellulose acetate butyrate, cellulose propionate, cellulose triacetate, cellulose triacetate, polyethylene, polyethylene-vinyl acetate copolymers, ionomers (ethylene polymers) polyethylene-nylon copolymers, polypropylene, methyl pentene polymers, polyvinyl fluoride, and aromatic polysulfones.

34. The method of claim 28, wherein the polymer film is polyethylene-terephthalate.

35. The method of claim 28, wherein the polymer film is optically transparent.

36. The method of claim 28, wherein the polymer film has an optical transparency between 5% and 95%.

37. The method of claim 28, wherein the polymer film has an optical transparency between approximately 20% and 80%.

38. The method of claim 28, wherein the self-assembling monolayer is formed from compounds with the following general formula:

X—R—Y wherein:

X is reactive with the metal or metal oxide on the polymer film;

R is a hydrocarbon chain; and

Y is a compound with any property of interest.

39. The method of claim 36, wherein:

X is a asymmetrical or symmetrical disulfide (—R'SSY', —RSSY), sulfide (—R'SY', —RSY), diselenide (—R'Se—SeY'), selenide (R'SeY', —RSeY), thiol (—SH), nitrile (—CN), isonitrile, nitro (—$NO_2$), selenol (—SeH), trivalent phosphorous compounds, isothiocyanate, xanthate, thiocarbamate, phosphine, thioacid or dithioacid, carboxylic acids, hydroxylic acids, and hydroxamic acids;

R and R' are hydrocarbon chains which may optionally be interrupted by hetero atoms, and which may optionally be perfluorinated, and which are preferably non-branched; and Y and Y' are hydroxy, carboxyl, amino, aldehyde, hydrazide, carbonyl, epoxy, or vinyl groups.

40. The method of claim 36, wherein R is greater than 7 carbon atoms in length.

41. The method of claim 36, wherein R is a compound of the form $(CH_2)_a$—Z—$(CH_2)_b$,, wherein a≧0, b≧7, and Z is any chemical functionality of interest.

42. The method of claim 36, wherein Z is selected from the group consisting of sulfones, lactams, and urea.

43. The method of claim 28, wherein there are two or more self-assembling monolayers with different chemical properties.

44. The method of claim 28, wherein a first self-assembling monolayer is hydrophobic, and a second self-assembling monolayer is hydrophilic.

45. The method of claim 28, wherein the analyte is bacteria, yeast, fungus, virus, rheumatoid factor, IgG, IgM, IgA and IgE antibodies, carcinoembryonic antigen, streptococcus Group A antigen, viral antigens, antigens associated with autoimmune disease, allergens, tumor antigens, streptococcus Group B antigen, HIV I or HIV II antigen, antibodies viruses, antigens specific to RSV,, an antibody, antigen, enzyme, hormone, polysaccharide, protein, lipid, carbohydrate, drug or nucleic acid, *Neisseria meningitides* groups A, B, C, Y and W sub 135, *Streptococcus pneumoniae, E. coli* K1, *Haemophilus influenza* type B, an antigen derived from microorganisms, a hapten, a drug of abuse, a therapeutic drug, an environmental agents, or antigens specific to Hepatitis.

46. The method of claim 43, wherein the analyte is bacteria, yeast, fungus or virus.

47. The method of claim 27, wherein the receptive material are antigens, antibodies, oligonucleotides, chelators, enzymes, bacteria, yeasts, fungi, viruses, bacterial pili, bacterial flagellar materials, nucleic acids, polysaccharides, lipids, proteins, carbohydrates, metals, hormones and receptors for said materials.

48. A method of detecting an analyte in a medium comprising:

contacting the medium suspected of containing the analyte with a biosensing device, the biosensing device comprising:

a polymer film coated with metal; and a self-assembling monolayer printed in a first, non-defracting pattern onto the polymer film wherein the self-assembling monlayer has a receptive material thereon that is specific for the analyte; and transmitting a light through the polymer film; and detecting the presence of the analyte bound to the receptive material by detecting a second pattern formed form by the diffraction of the transmitted light;

further wherein the analyte has a size of the same order as the wavelength of the transmitted light thereby resulting in the diffraction of the transmitted light.

49. The biosensor of claim 1, wherein the printed pattern diffracts the transmitted light such that the diffracted light has a minimum periodicity of ½ the wavelength and wherein the printed pattern has a refractive index different from a non-printed portion of the biosensor.

50. The method of claim 29, wherein the printed pattern diffracts the transmitted light such that the diffracted light has a minimum periodicity of ½ the wavelength and wherein the printed pattern has a refractive index different from a non-printed portion of the biosensor.

51. The biosensor of claim 1, wherein the diffraction pattern is visible to the unaided eye.

52. The method of claim 29, wherein the diffraction pattern is visible to the unaided eye.

* * * * *

UNITED STATES PATENT AND TRADEMARK OFFICE
CERTIFICATE OF CORRECTION

PATENT NO. : 5,922,550
DATED : July 13, 1999
INVENTOR(S) : Everhart et al.

Figure 6A:
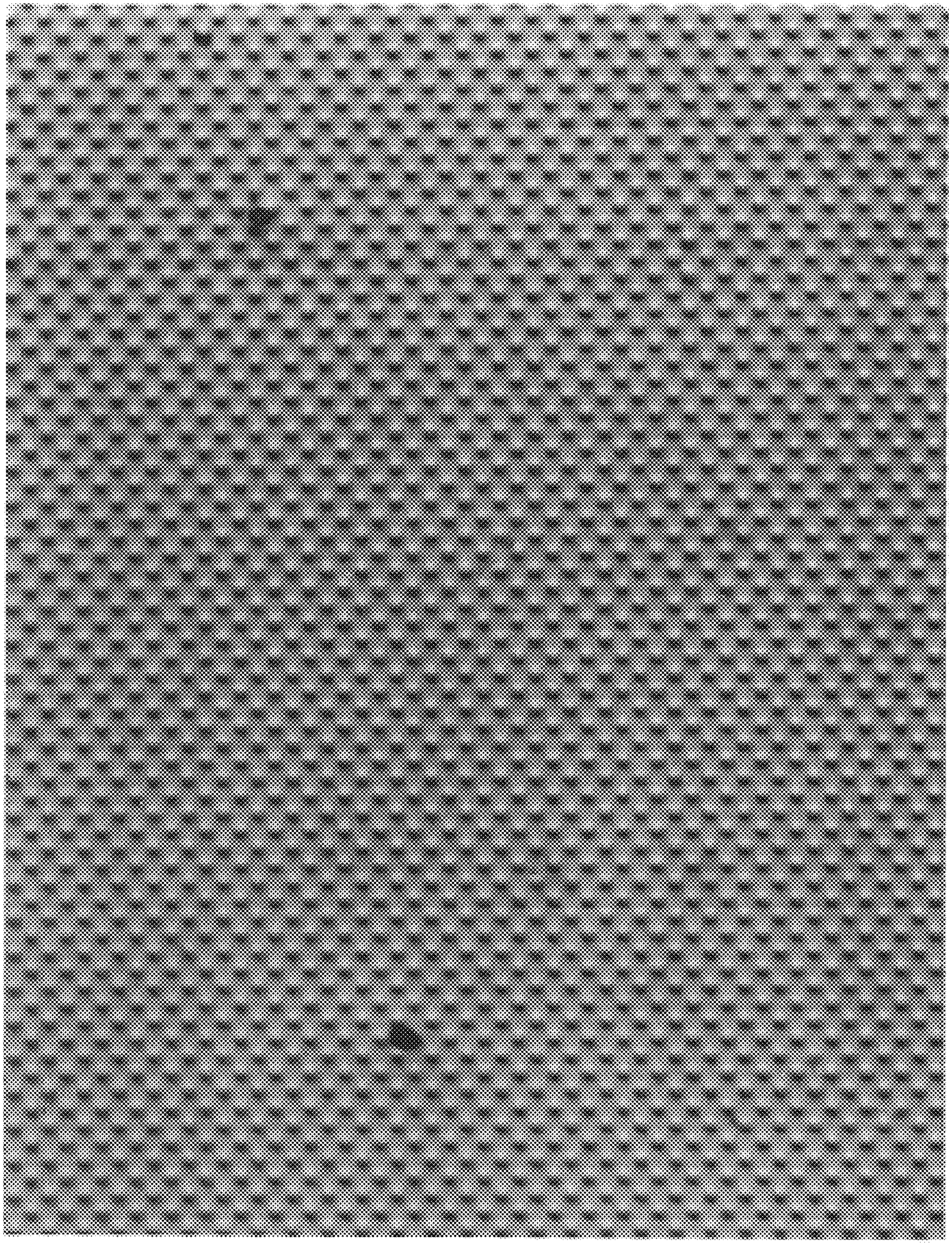
FIG. 6*a* is an optical photomicrograph at 300× magnification of 10 micron-diameter circles of hydrophilic self-assembling monolayers formed by printing of 16-mercaptohexadecanoic acid, as described in Example 1, below, and after exposure to a high surface energy, curable, optical adhesive. The adhesive was cured by ultraviolet light (UV) exposure.
Figure 6B:
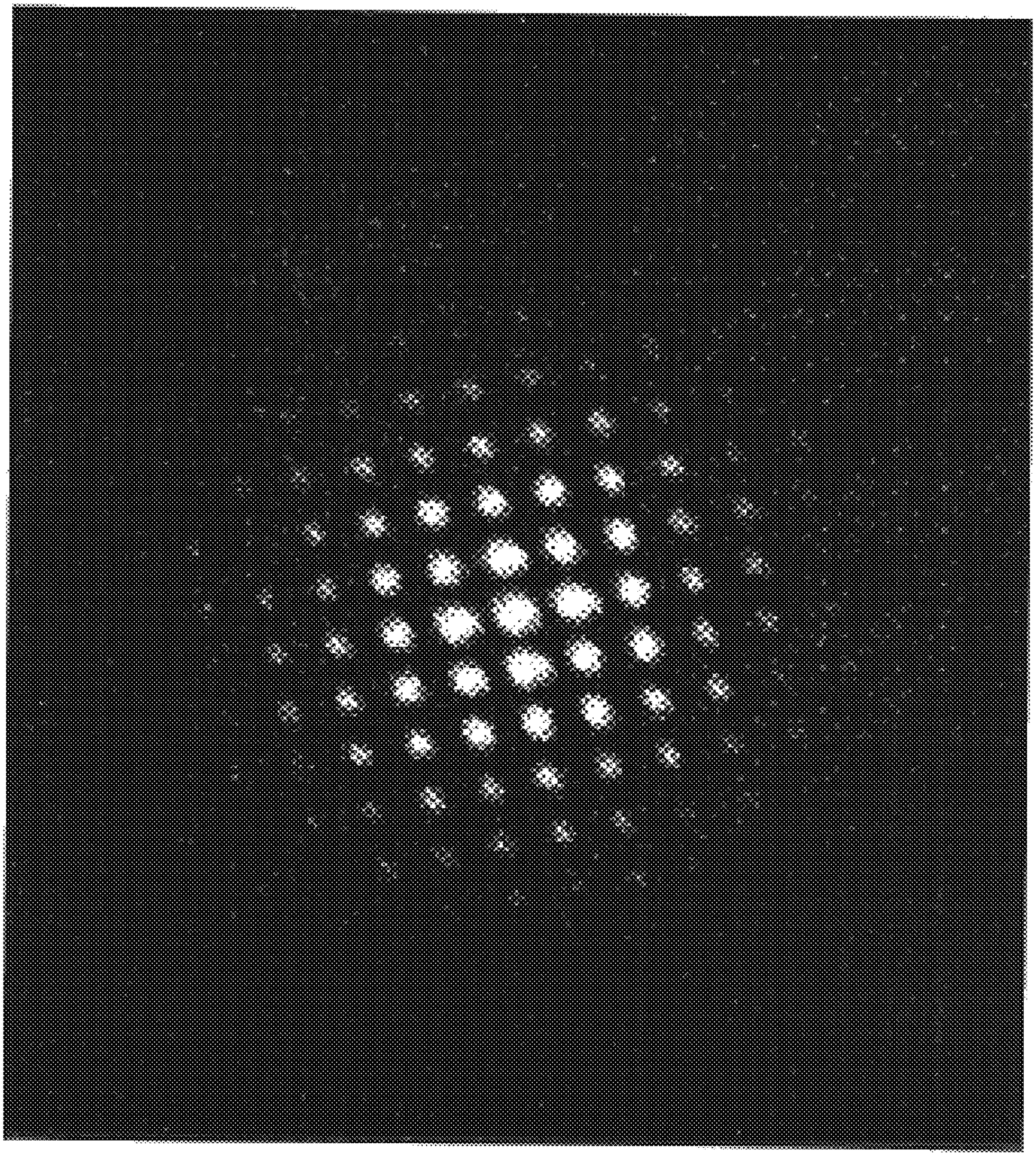
FIG. 6*b* is a photograph of the diffraction pattern formed by visible light transmitted through the self-assembling monolayer pattern described by FIG. 5*a*.
Figure 7:
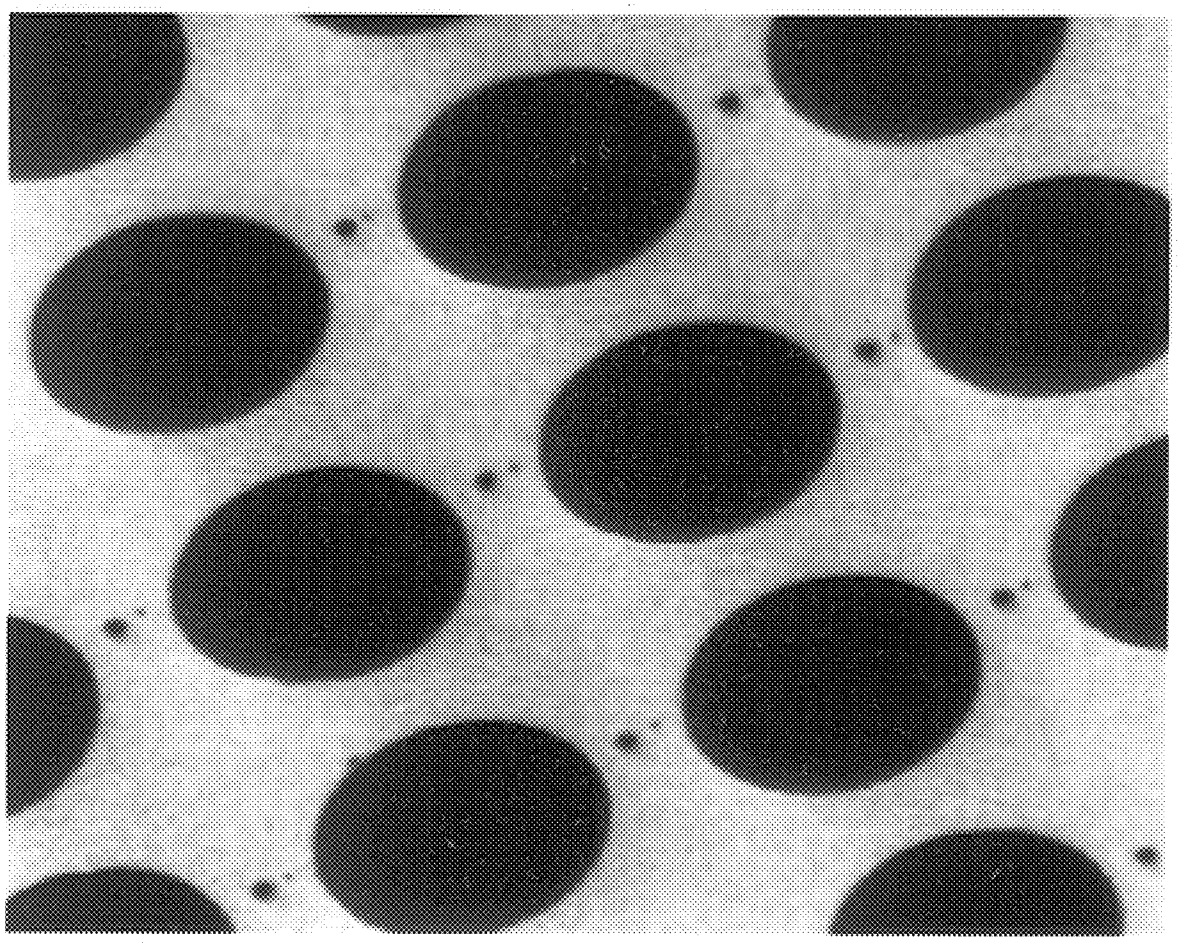
FIG. 7 is a field emission secondary electron micrograph image of 10 micron-diameter circles formed by printing of self-assembled photocurable polymers on hydrophilic self-assembling monolayers after exposure to a high surface energy, UV curable adhesive.
Figure 8A:
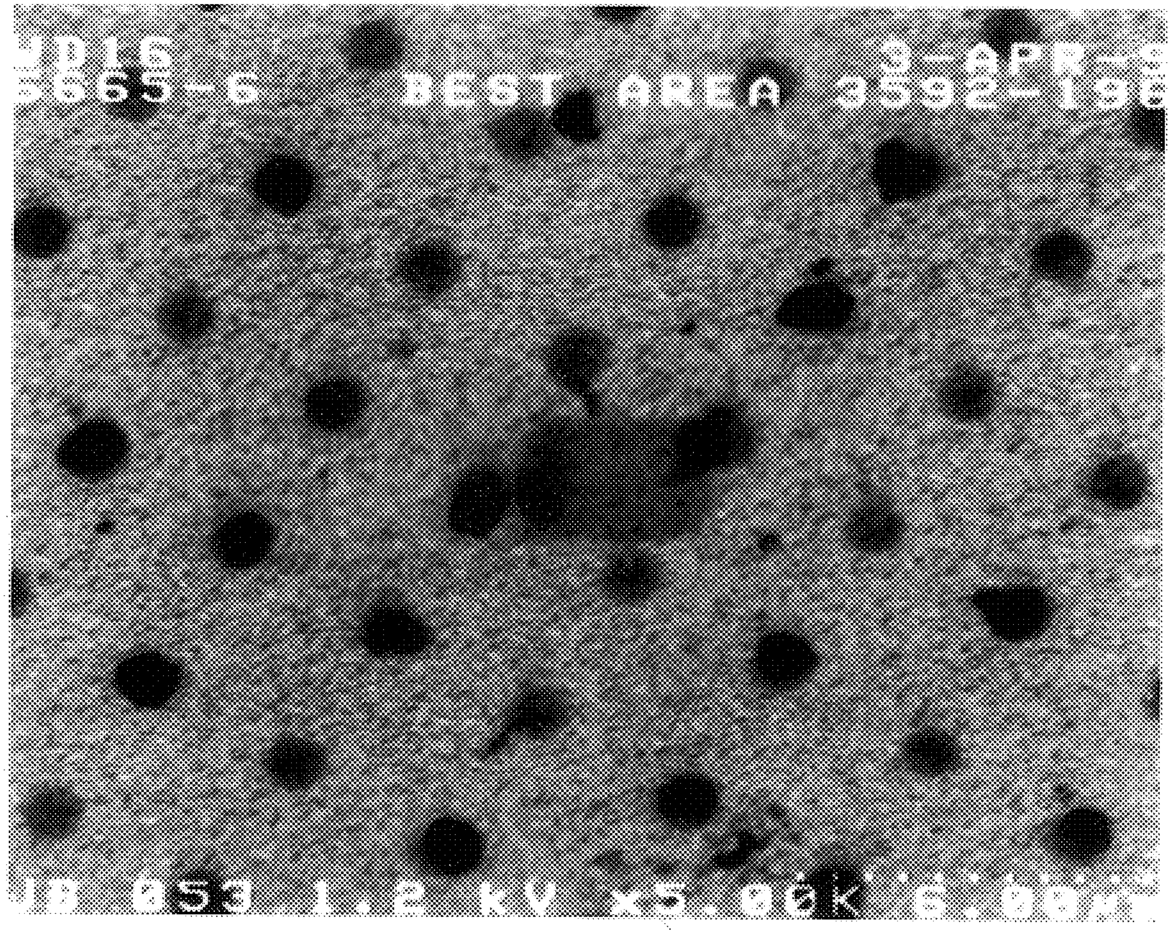
FIG. 8*a* and 8*b* are field emission secondary electron micrographs of 1.5 micron diameter circles of self-assembling monolayers printed onto gold-coated MYLAR®, as described in Example 1.
Figure 8B:
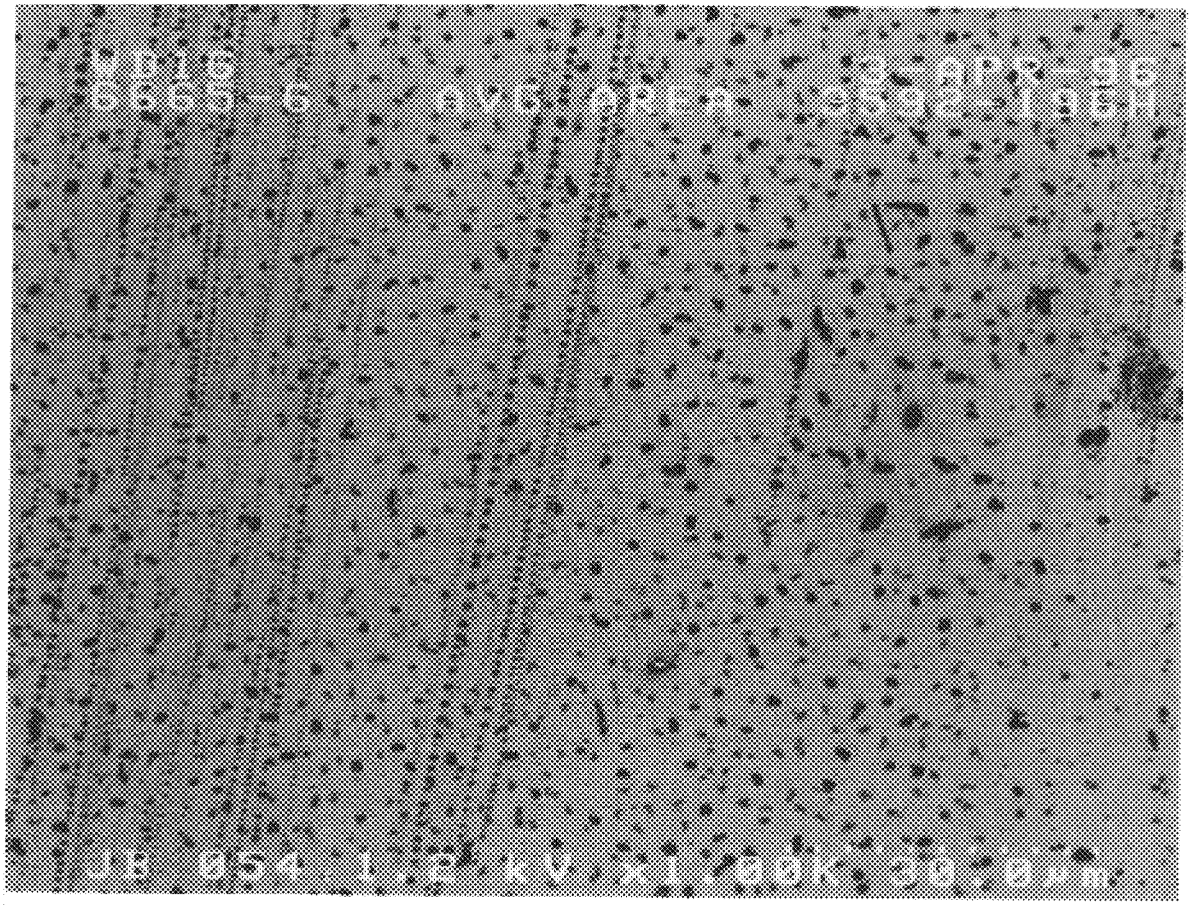

It is certified that error appears in the above-identified patent and that said Letters Patent is hereby corrected as shown below:

Column 4,
Line 24, please delete "Fig. 5a" and insert in place thereof -- FIG. 6a --

Column 7,
Line 54, please delete "lime" and insert in place thereof -- time --

Column 10,
Line 58, please delete one of the duplicate phrases of "cellulose triacetate,"

Column 14,
Line 57, after "designated $CH_3$" please insert a semicolon so that the phrase now reads "HS-$(CH_2)_{15}$-$CH_3$-designated $CH_3$; HS-$(CH_2)_{15}$COOH,-designated COOH"

Column 16,
Line 40, please delete one of the duplicate phrases of "cellulose triacetate,"

Column 17,
Line 1, please insert a hyphen in front of the second phrase of "(SeY')" so that the line now reads "SeY', selenide (-SeY', -SeY), thiol (-SH), nitrile"
Line 62, please delete "claim 26" and insert in place thereof -- claim 27 --

Column 20,
Line 12, please delete "form"

Signed and Sealed this

Twenty-third Day of October, 2001

*Attest:*

Nicholas P. Godici

NICHOLAS P. GODICI

*Attesting Officer* *Acting Director of the United States Patent and Trademark Office*